(12) United States Patent
Boggs et al.

(10) Patent No.: US 11,745,011 B2
(45) Date of Patent: *Sep. 5, 2023

(54) APPARATUS AND METHOD FOR POSITIONING, IMPLANTING AND USING A STIMULATION LEAD

(71) Applicant: SPR Therapeutics, Inc., Cleveland, OH (US)

(72) Inventors: Joseph W. Boggs, Chapel Hill, NC (US); Amorn Wongsarnpigoon, Chapel Hill, NC (US); Matthew G. deBock, Morrisville, NC (US); Meredith J. McGee, Cary, NC (US); Devin Sell, Brecksville, OH (US); Robert B. Strother, Willoughby Hills, OH (US)

(73) Assignee: SPR Therapeutics, Inc., Cleveland, OH (US)

( * ) Notice: Subject to any disclaimer, the term of this patent is extended or adjusted under 35 U.S.C. 154(b) by 18 days.

This patent is subject to a terminal disclaimer.

(21) Appl. No.: 17/458,664

(22) Filed: Aug. 27, 2021

(65) Prior Publication Data
US 2021/0386995 A1 Dec. 16, 2021

Related U.S. Application Data

(63) Continuation of application No. 15/388,128, filed on Dec. 22, 2016, now Pat. No. 11,103,697, which is a
(Continued)

(51) Int. Cl.
*A61N 1/05* (2006.01)
*A61N 1/36* (2006.01)
(Continued)

(52) U.S. Cl.
CPC ........ *A61N 1/0558* (2013.01); *A61B 17/3468* (2013.01); *A61N 1/0502* (2013.01);
(Continued)

(58) Field of Classification Search
None
See application file for complete search history.

(56) References Cited

U.S. PATENT DOCUMENTS 3,964,470 A   6/1976   Trombley
4,281,660 A   8/1981   Fujiwara
(Continued)

OTHER PUBLICATIONS

Patent Cooperation Treaty (PCT), International Search Repod and Written Opinion for Application PCT/US16/57267, dated Mar. 24, 2017, 43 pp., International Searching Authority, US.
(Continued)

*Primary Examiner* — Catherine M Voorhees
*Assistant Examiner* — Elizabeth K So
(74) *Attorney, Agent, or Firm* — McDonald Hopkins LLC

(57) ABSTRACT

An introducing device for locating a tissue region and deploying an electrode is shown and described. The introducing device may include an outer sheath. An inner sheath may be disposed within the outer sheath. The inner sheath may be configured to engage an implantable electrode. In an example, the inner sheath may comprise a stimulation probe having an uninsulated portion at or near a distal end of the delivery sheath. The outer sheath may be coupled to a power source or stimulation signal generating circuitry at a proximal end. A clinician may control application of the stimulation signal to a tissue region via the outer sheath.

13 Claims, 20 Drawing Sheets

Related U.S. Application Data continuation of application No. PCT/US2016/057267, filed on Oct. 17, 2016.

(51) Int. Cl.
  *A61B 17/34* (2006.01)
  *A61N 1/372* (2006.01)
  *A61N 1/378* (2006.01)

(52) U.S. Cl.
  CPC ....... *A61N 1/0551* (2013.01); *A61N 1/36017* (2013.01); *A61N 1/36071* (2013.01); *A61N 1/37205* (2013.01); *A61N 1/3787* (2013.01); *A61N 1/37211* (2013.01)

(56) References Cited

U.S. PATENT DOCUMENTS

| | | |
|---|---|---|
| 4,409,994 A | 10/1983 | Doring |
| 4,561,445 A | 12/1985 | Berke et al. |
| 5,571,162 A | 11/1996 | Lin |
| 5,776,178 A | 7/1998 | Pohndorf et al. |
| 5,871,532 A | 2/1999 | Schroeppel |
| 6,454,758 B1 | 9/2002 | Thompson et al. |
| 6,613,014 B1 | 9/2003 | Chi |
| 7,187,982 B2 | 3/2007 | Seifert et al. |
| 7,418,298 B2 | 8/2008 | Shiroff et al. |
| 7,749,225 B2 | 7/2010 | Carter |
| 7,848,821 B1 | 12/2010 | Ryu et al. |
| 7,949,395 B2 | 5/2011 | Kuzma |
| 8,313,339 B2 | 11/2012 | Monier |
| 9,427,574 B2 | 8/2016 | Lee et al. |
| 9,561,053 B2 | 2/2017 | Bonde et al. |
| 11,103,697 B2 * | 8/2021 | Boggs ................ A61B 17/3468 |
| 11,413,450 B2 * | 8/2022 | Boggs, II ........... A61N 1/37241 |
| 2001/0025092 A1 | 9/2001 | Gerber et al. |
| 2001/0025192 A1 | 9/2001 | Gerber |
| 2003/0225361 A1 | 12/2003 | Sabra |
| 2003/0229360 A1 | 12/2003 | Gayton |
| 2004/0260312 A1 | 12/2004 | Magnusson et al. |
| 2005/0033393 A1 | 2/2005 | Daglow |
| 2005/0113900 A1 | 5/2005 | Shiroff et al. |
| 2005/0240238 A1 | 10/2005 | Mamo et al. |
| 2006/0074412 A1 | 4/2006 | Zerfas et al. |
| 2007/0021786 A1 | 1/2007 | Parnis et al. |
| 2007/0255368 A1 | 11/2007 | Bonde et al. |
| 2008/0300618 A1 | 12/2008 | Gertner |
| 2010/0082087 A1 | 4/2010 | Silipo et al. |
| 2011/0218529 A1 | 9/2011 | Garcia |
| 2012/0035685 A1 | 2/2012 | Saha et al. |
| 2012/0197388 A1 | 8/2012 | Khairkhahan et al. |
| 2014/0288616 A1 | 9/2014 | Rawat et al. |
| 2016/0250466 A1 | 9/2016 | Boggs et al. |
| 2016/0361535 A1 | 12/2016 | Perryman et al. |

OTHER PUBLICATIONS

European Patent Office Communication, Extended European Search Repod relating to Application No. 16856384.9, dated May 4, 2019, 8 pages.

* cited by examiner

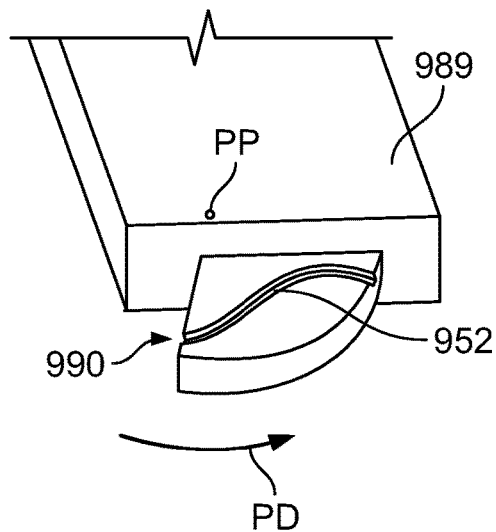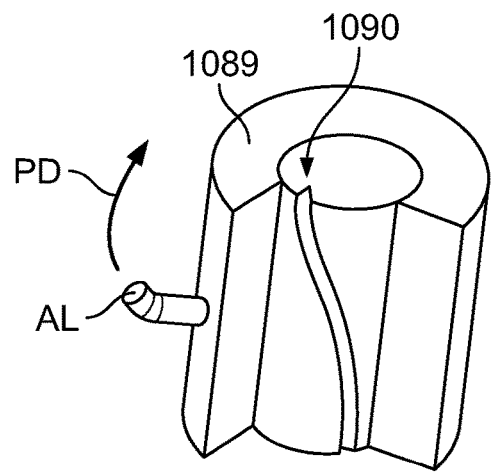
FIGURE 21A
FIGURE 21B
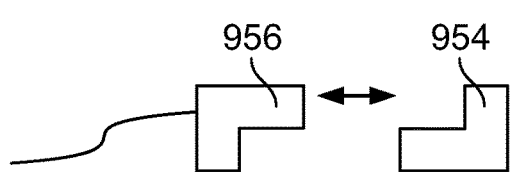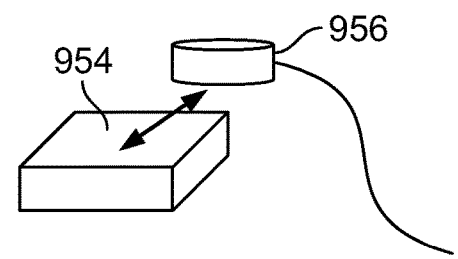
FIGURE 22A
FIGURE 22B

APPARATUS AND METHOD FOR POSITIONING, IMPLANTING AND USING A STIMULATION LEAD

CROSS REFERENCE TO RELATED APPLICATIONS

This application is continuation of and claims priority U.S. Utility application Ser. No. 15/388,128 filed on Dec. 22, 2016, which is now U.S. Pat. No. 11,103,697 and which is a continuation of and claims priority to International Patent Application Serial Number PCT/US16/57267 filed on Oct. 17, 2016 which, in turn, claimed priority to U.S. Patent Application Ser. No. 62/242,205 filed on Oct. 15, 2015. The disclosure of these applications, along with any other United States Patents and United States Patent Publications identified in this specification, are hereby incorporated by reference.

FIELD OF INVENTION

The present disclosure generally relates to locating a target tissue and deployment of a lead, and, more particularly, the disclosure relates to a system, apparatus, and methods for locating a target tissue region and deploying a lead via a single handheld device.

BACKGROUND

Electrical stimulation systems have been used for the relief of chronic and acute pain as well as many other medical uses. There exist both external and implantable devices for providing electrical stimulation to activate nerves and/or muscles to provide therapeutic treatments. These "neurostimulators" are able to provide treatment and/or therapy to individual portions of the body. The operation of these devices typically includes the use of one or more electrodes placed either on the external surface of the skin or a surgically implanted lead with one or more electrodes. In many cases, surface electrode(s), cuff-style electrode(s), paddle-style electrode(s), or epidural-style or cylindrical-style electrodes and/or leads may be used to deliver electrical stimulation to the select portion of the patient's body.

In some systems, an electrode(s) may be inserted into a body percutaneously. In these systems an electrode or a plurality of electrodes may be operatively positioned on a lead that is percutaneously inserted into a patient. There exists a need for several device improvements relating to the positioning and deployment capabilities of electrode leads used in various medical capacities, including electrical stimulation systems.

As described extensively in the literature, the existing systems and devices for peripheral nerve stimulation may not meet the needs of the clinicians and patients. Existing systems can be inefficient; time consuming; and too invasive. They may also require prohibitively extensive training and skill to use; exhibit (or contribute to) poor device performance/failure and suboptimal efficacy/effectiveness/safety; and prohibit use in patients and clinical settings that could benefit from electrical stimulation. In view of these deficiencies, there is a large and unmet need for a device(s), system(s), and method(s) that enables safe, effective, reliable, easy to use, and minimally-invasive delivery of electrical stimulation lead(s) for the treatment of pain and other conditions.

Some conventional systems for electrode deployment or implantation comprise two entirely separate procedures and devices—first a test needle and then a second introducer/electrical lead. These systems, with two separate steps, may be inefficient, time consuming, and not ideal for patients as this may require two separate needle insertions. Further, clinicians have also reported a need to view which direction a lead anchor of an electrode is facing once an introducer has been inserted into a tissue of a patient. This viewing capability may aid in the effective deployment of the lead and improve the efficiency of the procedure. These systems rely upon carrying the lead within a single needle and deploying that needle by expelling the lead out of the open end of the needle. Owing to the relatively fragile nature of the lead itself, the ability to adjust the positioning of the lead—even small amounts—is quite limited.

Another system is described in United States Patent Publication No. 2007/0255368. Here, a coiled lead is placed in its desired location via a small diameter needle. The lead is carried in the needle, and it has a tines or sutures made of non-conductive material that expand after the lead is deployed out of the needle. The tines/sutures secure the lead in its desired location, but repositioning of the lead during the insertion process is difficult, if not impossible, owing to the lead's positioning in the needle and the non-conductive nature of its tines/sutures. Further, movement or removal of the lead after it is deployed will cause tissue damage and disruption.

In view of the foregoing, a need exists for an improved system for electrode deployment or implantation that allows for test stimulation and repositioning of the lead during positioning.

SUMMARY OF INVENTION

A wide variety of inter-related aspects of the invention are described. The features of any one specific embodiment disclosed or depicted herein may be applied to other embodiments, and additional features and aspects of the system may be understood by those having skill in this field.

One aspect of the invention, an introducer system, has any combination of the following features:
a electrical stimulus generator unit;
a needle assembly having an axial length, the needle assembly including an outer sheath with a distal opening and an inner deployment mechanism;
a stimulation electrode made from an electrically conductive material, the electrode including a distal end having a bent anchor portion and a terminal end and a proximal end in communication with the stimulus generator unit;
wherein the bent anchor portion protrudes partially from the distal opening and the terminal end is held within the needle assembly between the inner deployment mechanism and an inner facing of the outer sheath;
wherein inner deployment mechanism is positionable along the axial length relative to the outer sheath so as to: (i) permit free movement between a proximal, protected position in which the electrode is substantially contained within the needle assembly and a test position in which the bent anchor portion protrudes sufficiently to deliver test stimulation from the stimulus generator unit while the terminal end remains within the needle assembly; and (ii) deploy the electrode at a final, distal position so that the terminal end is released out of the needle assembly;

wherein the inner deployment mechanism comprises an inner sheath having a terminal opening with a first edge engaging the partially protruding bent anchor portion;

wherein the inner sheath includes an aperture positioned proximally from the terminal opening and wherein the aperture has a second edge engaging the partially protruding bent anchor portion;

wherein at least one of the first edge and the second edge is fully rounded;

wherein the first edge is fully rounded;

wherein a groove extends between the terminal opening and the aperture and wherein at least a portion of the partially protruding bent anchor fits within the groove to minimize an outer diameter in a distal portion of the needle assembly;

wherein the outer diameter in the distal portion of the needle assembly at the distal end is substantially similar to an outer diameter at a second point along the axial length of the needle assembly;

wherein the terminal opening includes a bevel;

wherein a portion of the distal end of the outer sheath is thinned to accommodate the partially protruding bent anchor portion;

wherein the thinned portion comprises a groove;

wherein the inner deployment mechanism includes a stylet;

wherein the outer sheath includes a slot running along the axial length of the outer sheath defined at its proximal end by the distal opening;

wherein the partially protruding bent anchor portion moves through the slot when the inner deployment mechanism is repositioned from the proximal, protected position and the test position;

a quick disconnection mechanism for maintaining contact between the electrode and the stimulus generator unit;

wherein the quick disconnection mechanism includes at least one aperture or slot and wherein a proximal end of the electrode is received in the aperture or slot;

wherein the quick disconnection mechanism includes at least one magnet;

wherein the quick disconnection mechanism includes an insulation displacement connector;

wherein the quick disconnection mechanism includes at least one biasing member;

a positioning block selectively coupled to the needle assembly at an adjustable angle and rotation, the positioning block selectively attachable to a subject to facilitate insertion, repositioning, and test stimulation of the introducer system;

wherein the positioning block includes at least one adhesive facing;

wherein the positioning block includes a locking mechanism selectively inhibiting changes to at least one of the adjustable angle and the rotation;

a user control connected to the stimulus generator unit;

wherein the user control includes a graphical user interface;

wherein the user control is wirelessly connected to the stimulus generator unit;

wherein the needle assembly includes a spacer;

wherein the spacer is removable;

wherein the spacer moves in the axial length so as to retract at least the outer sheath;

wherein the electrode comprises a coiled or helical structure;

wherein the coiled or helical structure promotes tissue ingrowth;

wherein the inner deployment mechanism comprises a stylet at least partially positioned on an inner-most portion of the coiled or helical structure;

wherein the electrode comprises a biosorbable material;

wherein the bent anchor portion comprises the biosorbable material;

wherein the proximal end of the stimulation electrode is integrally coupled to a distal portion of a lead and wherein a proximal portion of the lead is in communication with the stimulus generating unit;

wherein the lead further comprises electrically insulating material;

at least one test electrode positioned on the outer sheath;

a plurality of test electrodes positioned on the outer sheath;

wherein the at least one test electrode is in communication with the stimulus generator unit;

wherein the plurality of test electrodes are positioned along the axial length of the outer sheath at spaced-apart intervals; and wherein stimulation can be delivered through each of the test electrodes individually, in concert, and/or in any combination.

Another aspect contemplates a method for delivering stimulation to a peripheral nerve system comprising any combination of the following:

attaching a stimulation electrode having a conductive distal anchor to an inner deployment mechanism, including bending a portion of the electrode including the distal anchor around a distal end of the inner deployment mechanism;

positioning the electrode and inner deployment mechanism within an outer sheath to create a two-part needle assembly;

connecting a proximal end of the needle assembly to a stimulus generator unit;

inserting a distal end of the needle assembly into a peripheral region of a human subject;

exposing the distal anchor to tissue in the human subject and delivering test stimulation through the electrode to provide therapy;

deploying the distal anchor and removing the needle assembly;

repositioning the needle assembly before deploying the distal anchor to maximize therapeutic effects;

wherein the connecting the proximal end of the needle assembly to stimulus generator unit includes creating at least one breakaway connection in between the electrode and the stimulus generator unit;

providing the human subject with a controller unit to optimize at least one of: the delivering the test stimulation and subsequent delivery of therapy after deploying the distal anchor;

wherein the electrode is a coiled or helical structure having an inner diameter and the inner deployment mechanism is provided in an inner-most portion of the coiled or helical electrode;

wherein the electrode is provided within an inner lumen of the inner deployment mechanism;

wherein the lumen includes an aperture proximate to but not in communication with an opening at the distal end of the lumen and wherein the electrode is threaded through the aperture so that the distal end is positioned between the inner deployment mechanism and an inner facing surface of the outer sheath; and wherein the distal anchor is exposed by advancing the inner lumen relative to the outer sheath and into the tissue but without releasing the distal anchor from the needle assembly.

A further aspect considers an introducer system having any combination of the following features:
- a electrical stimulus generator unit;
- a needle assembly having an axial length and an outer circumference, the needle assembly including an outer sheath with a distal opening, an inner deployment mechanism carried within the outer sheath, and at least one test electrode positioned along the outer circumference;
- a stimulation electrode having a distal anchor and a proximal end in communication with the stimulus generator unit, the electrode carried within the needle assembly;
- wherein the at least one test electrode delivers test stimulation from the stimulus generator unit without deploying the distal anchor;
- wherein a portion of the electrode on or immediately proximate to the distal anchor protrudes out of the inner deployment mechanism and serves as the test electrode;
- a slot positioned along the axial length of the needle assembly so that the test electrode protrude through the slot;
- wherein the inner deployment mechanism includes a plunger moving along the axial length in concert with the test electrode;
- a locking mechanism to prevent additional movement of the test electrode prior to final deployment of the distal anchor and the removal of the needle assembly; and
- wherein a plurality of test electrodes are positioned on the outer circumference.

A still further aspect considers an introducer system having any combination of the following features:
- a electrical stimulus generator unit;
- a needle assembly having a length-wise axis, the needle assembly including an outer sheath with a distal opening and an inner sheath with a deployment mechanism;
- a helical, open-coiled stimulation electrode made from an electrically conductive material, the electrode including a terminal end having a conductive anchor portion and a proximal end communicating with the stimulus generator unit;
- wherein the terminal end and at least a portion of the conductive anchor portion are held within the needle assembly between the inner sheath and an inner surface of the outer sheath;
- wherein the deployment mechanism and the outer sheath are selectively movable in concert and in opposing directions along the length-wise axis between a proximal protected position in which the electrode is completely contained within the outer sheath and a mid-point, test position in which the conductive anchor portion protrudes through the distal opening to deliver test stimulation from the stimulus generator unit while the terminal end remains within the needle assembly;
- wherein the conductive anchor portion and terminal end are released out of the needle assembly when the deployment mechanism and outer sheath are moved in opposing directions to a releasing, distal position and subsequently retracted in concert;
- wherein all of the bent anchor is held within the needle assembly; and
- wherein at least one of the mid-point, test position and the releasing, distal position include rotation of the inner sheath relative to the outer sheath about the length-wise axis so as to cause the conductive anchor portion to protrude through an aperture in the outer sheath positioned proximate to the distal opening.

Yet another aspect considers an introducer system having any combination of the following features:
- a electrical stimulus generator unit;
- a needle assembly having a length-wise axis, the needle assembly including an outer sheath with a distal opening and an inner stylet moving freely within the outer sheath;
- a helical, open-coiled stimulation electrode made from an electrically conductive material, the electrode detachably connected to the inner stylet and including a terminal end having a conductive anchor portion and a proximal end communicating with the stimulus generator unit;
- wherein the terminal end and at least a portion of the conductive anchor portion are held within the outer sheath;
- wherein the inner stylet and the outer sheath are selectively movable in concert and in opposing directions along the length-wise axis between a proximal protected position in which the electrode is completely contained within the outer sheath and a mid-point, test position in which the conductive anchor portion protrudes through the distal opening to deliver test stimulation from the stimulus generator unit while the terminal end remains within the needle assembly;
- wherein the conductive anchor portion and terminal end are released out of the needle assembly when the inner stylet and outer sheath are moved in opposing directions to a releasing, distal position and subsequently retracted in concert;
- wherein the stylet is positioned within an inner-most portion of the helical, open-coiled electrode;
- wherein all of the bent anchor is held within the needle assembly; and
- wherein at least one of the mid-point, test position and the releasing, distal position include rotation of the inner sheath relative to the outer sheath about the length-wise axis so as to cause the conductive anchor portion to protrude through an aperture in the outer sheath positioned proximate to the distal opening.

A further aspect considers an introducer system having any combination of the following features:
- an electrical stimulus generator unit;
- a needle assembly including an outer sheath with a distal opening, an inner deployment mechanism carried within the outer sheath, and at least one test electrode positioned along an outer circumference of the needle assembly and communicating with the stimulus generator unit;
- a stimulation lead comprising a monopolar electrode forming a portion of a selectively deployable anchor at a distal end of the lead, the stimulation lead communicating with the stimulus generator unit;
- wherein the monopolar electrode comprises a plurality of mechanically integrated strands of an electrically conductive material wound together in the form of a helix having a central void space;
- wherein the needle assembly is inserted into a patient and optionally repositioned based upon the at least one test electrode delivering test stimulation from the stimulus generator unit until an optimal location is identified;
- wherein, when the inner deployment mechanism is moved relative to the outer sheath, the distal end releases out of the needle assembly and the deployable anchor is fixed at the optimal location to deliver regular stimulation from the stimulus generator unit to the optimal location;

wherein a plurality of test electrodes are positioned along the outer circumference;

wherein the test stimulation is delivered by the plurality of electrodes to identify the optimal location without repositioning the needle assembly and wherein the inner deployment mechanism is moved to position the deployable anchor at the optimal location when the needle assembly is retracted out of the patient;

wherein the deployment mechanism comprises an inner sheath;

wherein the deployable anchor protrudes out of a distal opening in the inner sheath and wherein the distal end is positioned between the inner and outer sheaths prior to the release of the distal end; and wherein at least a portion of the deployment mechanism is carried in the central void.

One aspect considers an introducer system having any combination of the following features:

an electrical stimulus generator unit;

a needle assembly having an axial length and an outer circumference, the needle assembly including an outer sheath with a distal opening, an inner sheath or an inner stylet deployment mechanism carried within the outer sheath, and at least one test electrode positioned along the outer circumference and capable of electrically communicating with the stimulus generator unit;

a helical, open-coil stimulation lead made from an electrically conductive material at least partially covered by an electrically insulating material and having an electrode including a coiled section of electrically conductive material formed into a mechanical anchor at a terminal end coupled to the distal end of the lead, and the lead also having a proximal end capable of electrically communicating with the stimulus generator unit; and wherein the at least one test electrode delivers test stimulation from the stimulus generator unit without deploying the distal anchor and allowing the entire needle assembly to be fully re-positionable until the terminal end is released from the needle assembly.

A final aspect considers an introducer system having any combination of the following features:

an electrical stimulus generator unit;

a needle assembly having an axial length and an outer circumference, the needle assembly including an outer sheath with a distal opening, an inner deployment mechanism carried within the outer sheath, and at least one test electrode positioned along the outer circumference and capable of electrically communicating with the stimulus generator unit;

a stimulation lead made from an electrically conductive material and an electrically insulating material and having an electrode including a bent anchor portion at a terminal end coupled to a distal end of the lead, and the lead including a proximal end capable of electrically communicating with the stimulus generator unit; and wherein the at least one test electrode delivers test stimulation from the stimulus generator unit without deploying the distal anchor.

While individual aspects of the invention are recited above, it is possible to couple specific features and limitations associated with one aspect to that of another aspect. Further, the functions and actions associated with the method aspect may further inform the structural features of apparatus aspects noted herein. Any of these foregoing features may form the basis for subsequent claims to still further aspects of the invention, even though all of those aspects may not be individually recited herein.

BRIEF DESCRIPTION OF THE DRAWINGS

Operation of the invention may be better understood by reference to the detailed description taken in connection with the following illustrations. These appended drawings form part of this specification, and written information in the drawings should be treated as part of this disclosure. In the drawings.

Figure 4:
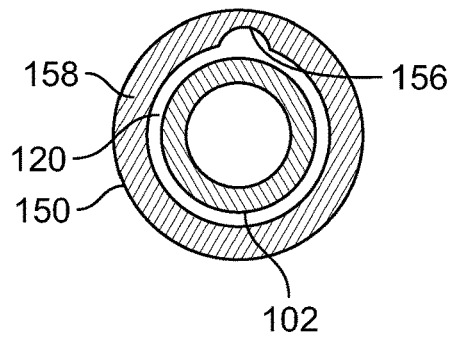
Figure 5:
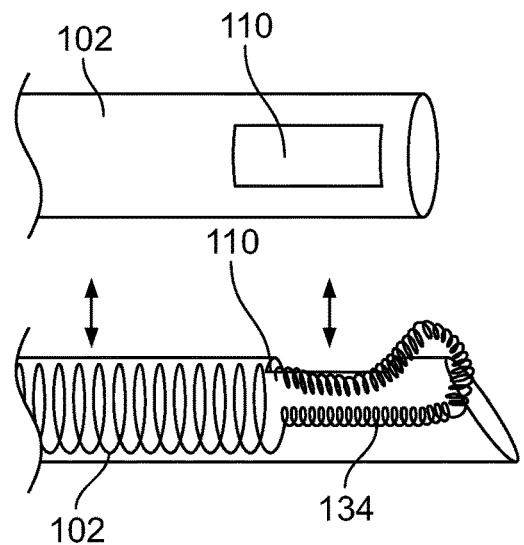
Figure 6:
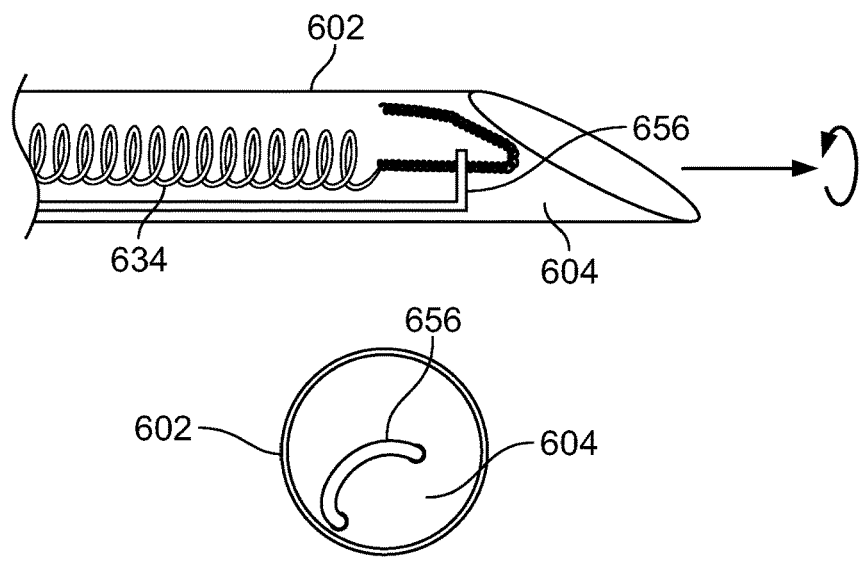
Figure 7A:
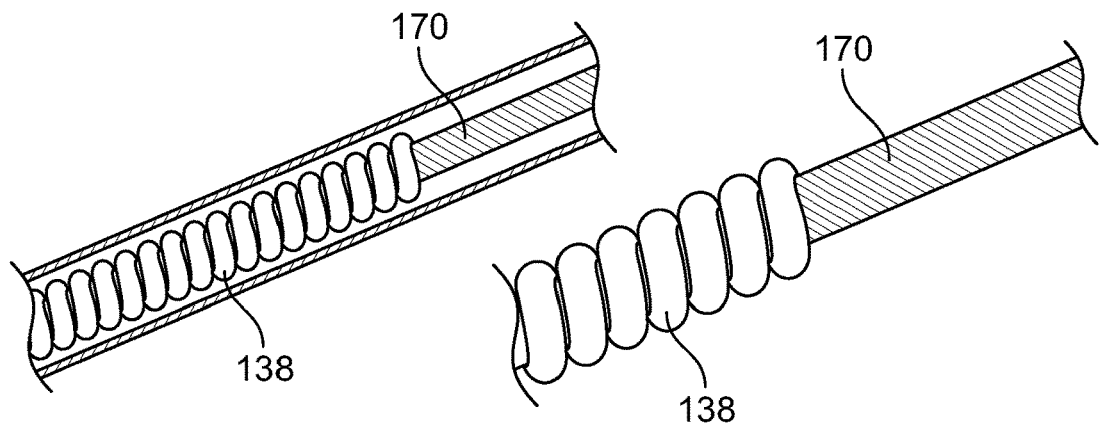
Figure 8:
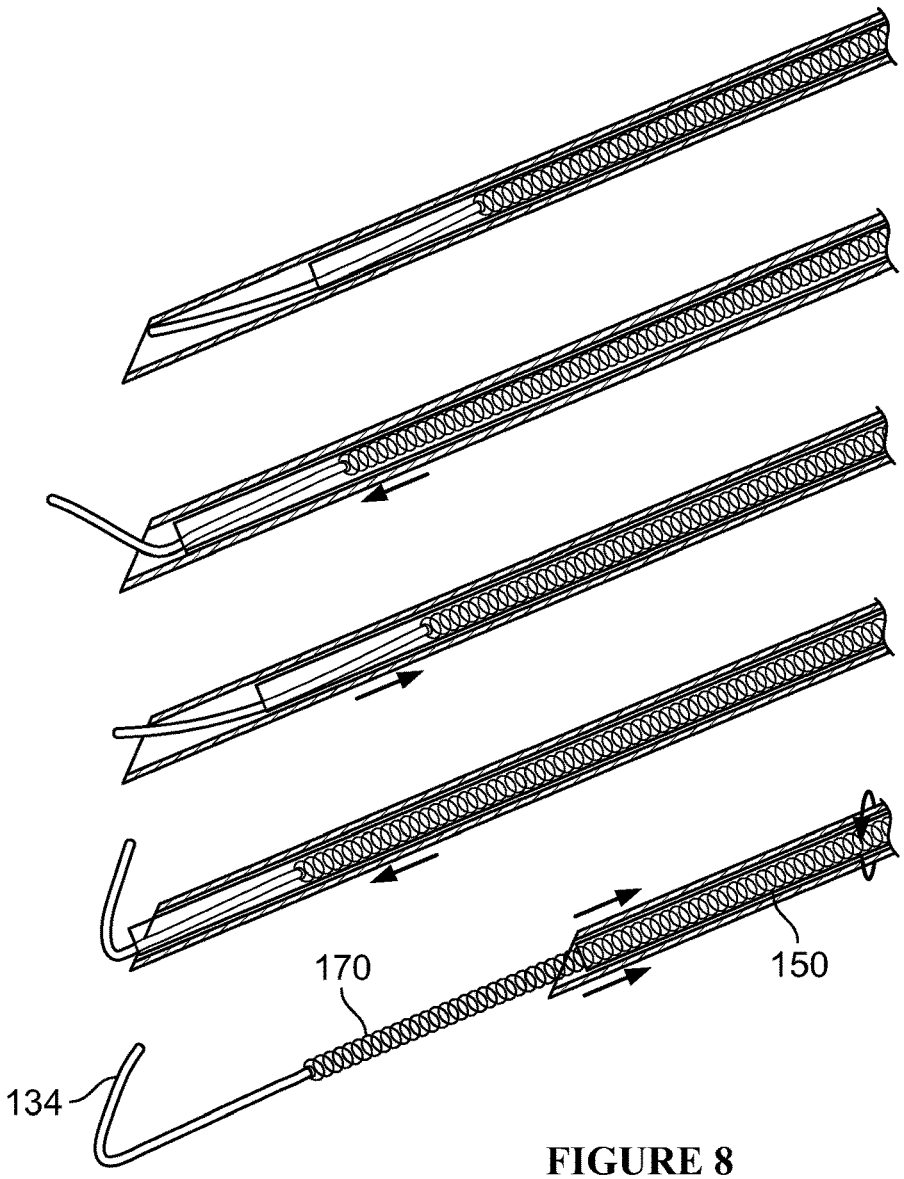
Figure 9A:
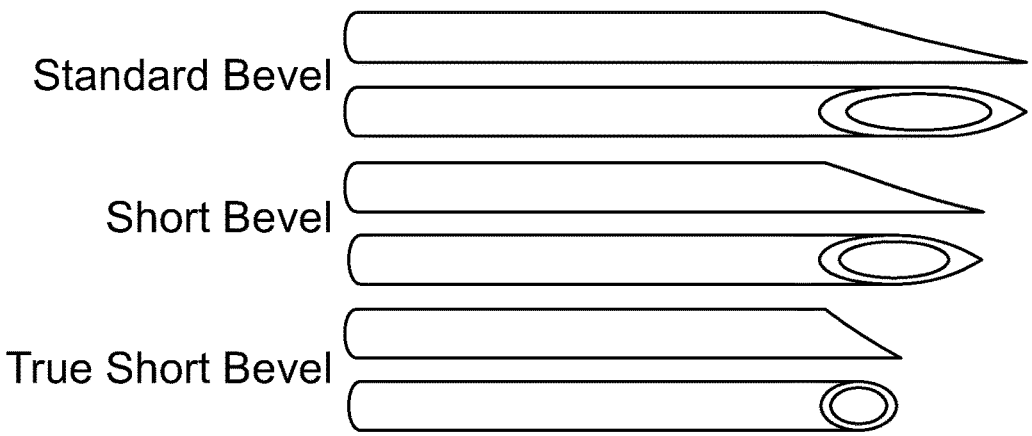
Figure 9B:
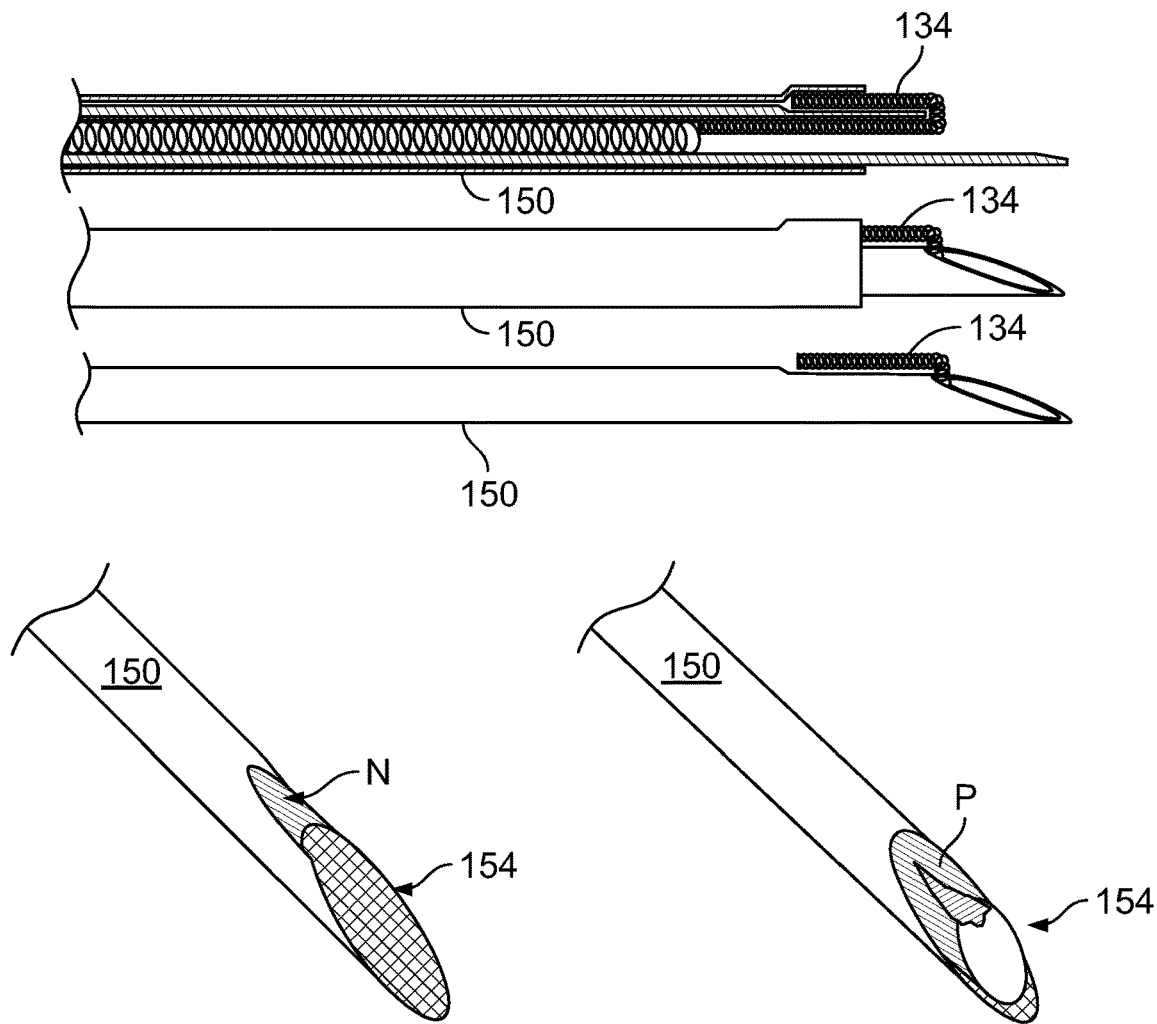
Figure 9C:
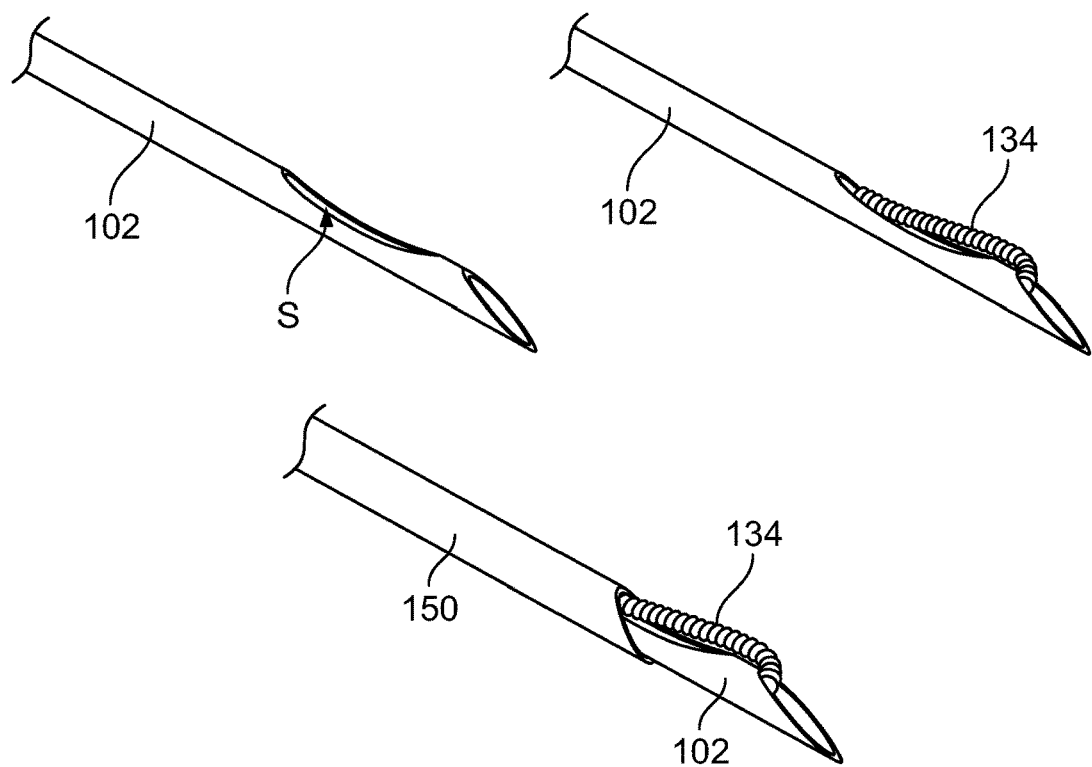
Figure 9D:
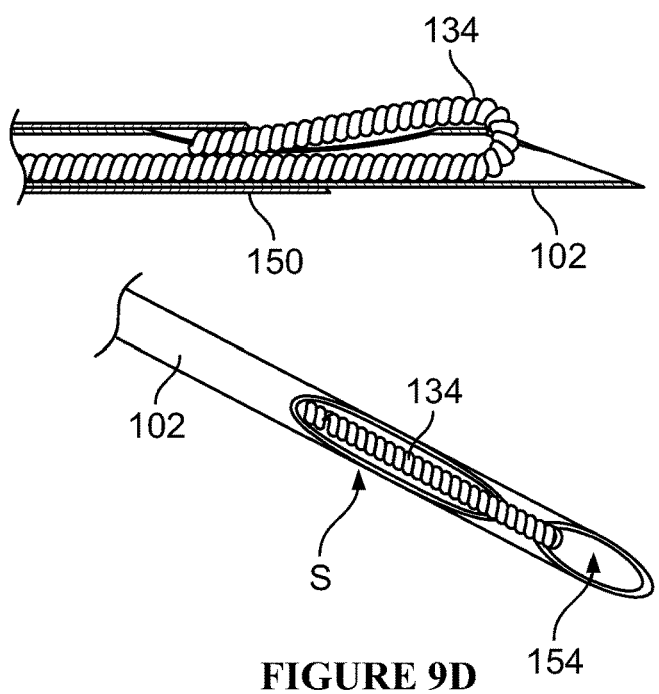
Figure 10:
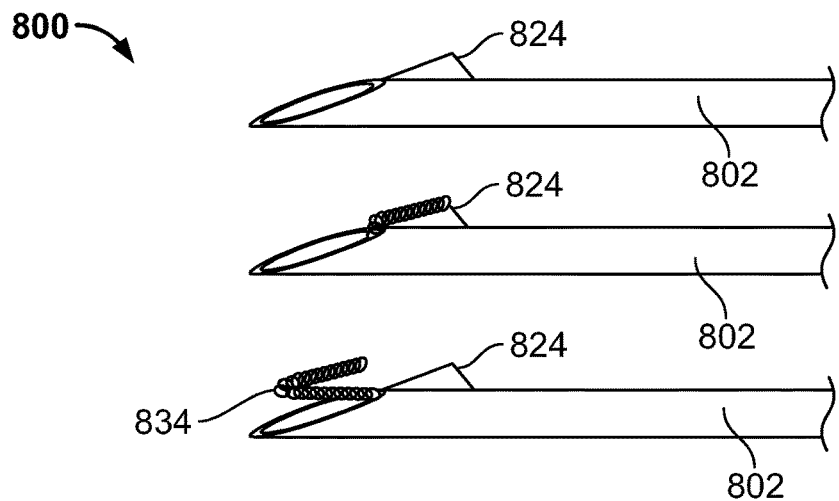
Figure 11:
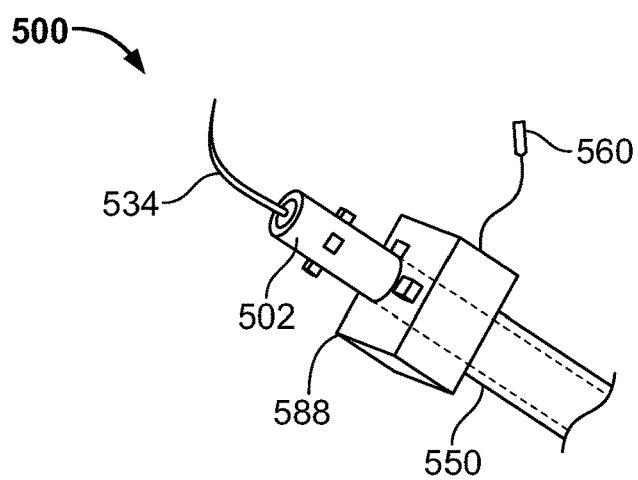
Figure 12A:
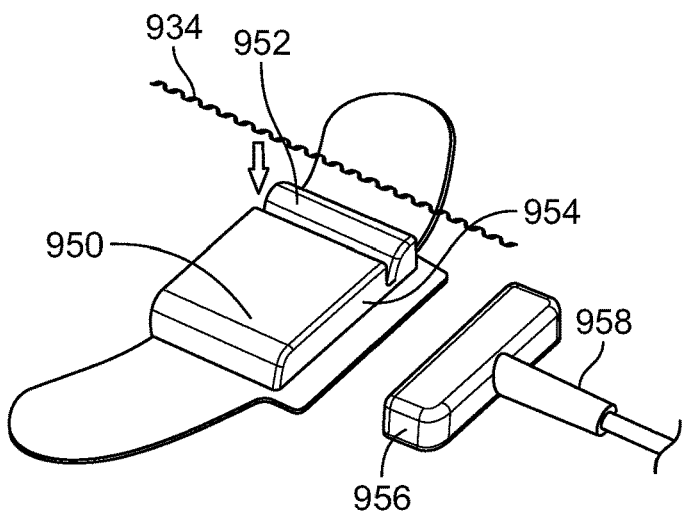
Figure 12B:
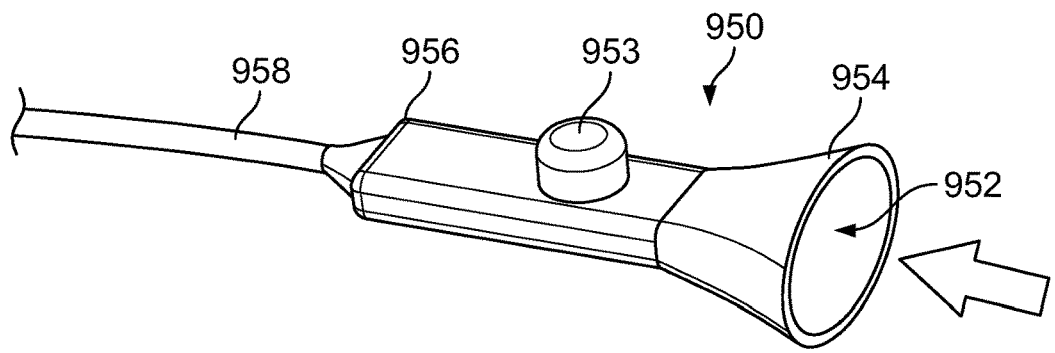
Figure 13:
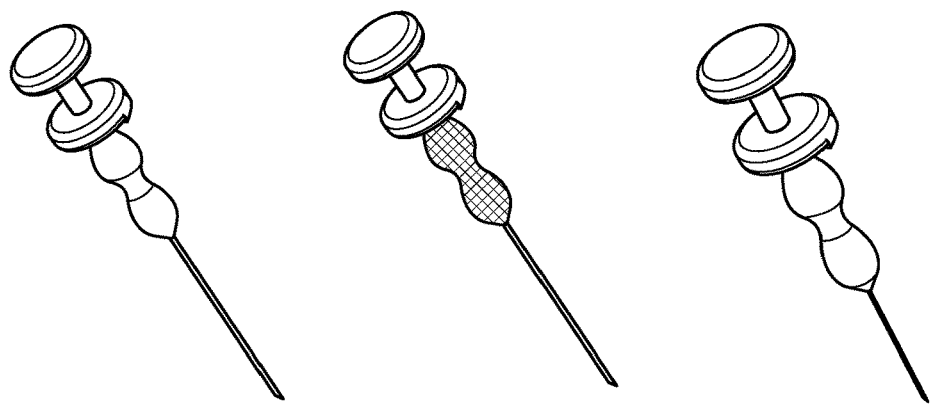
Figure 15A:
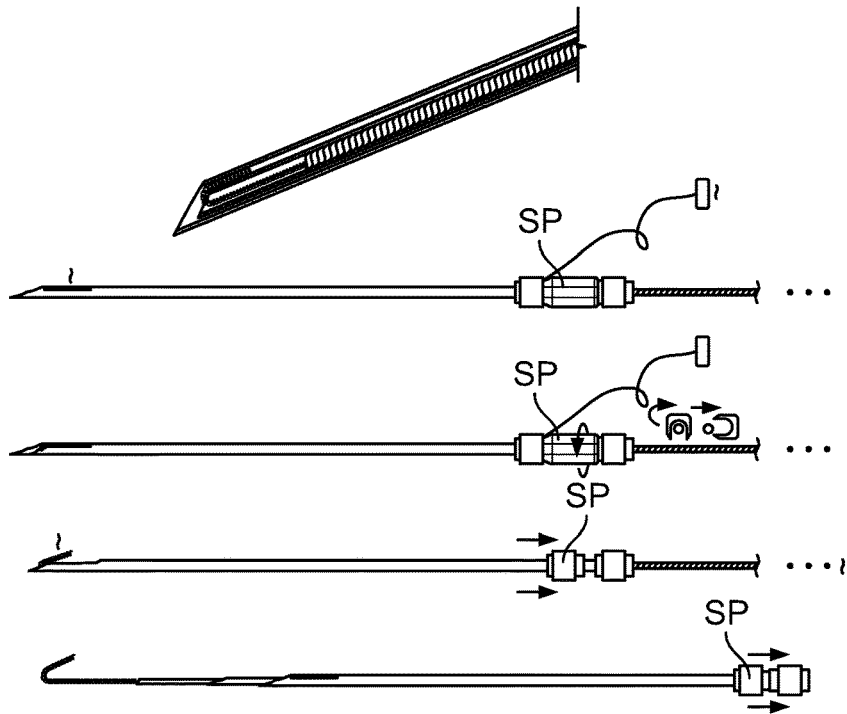
Figure 15B:
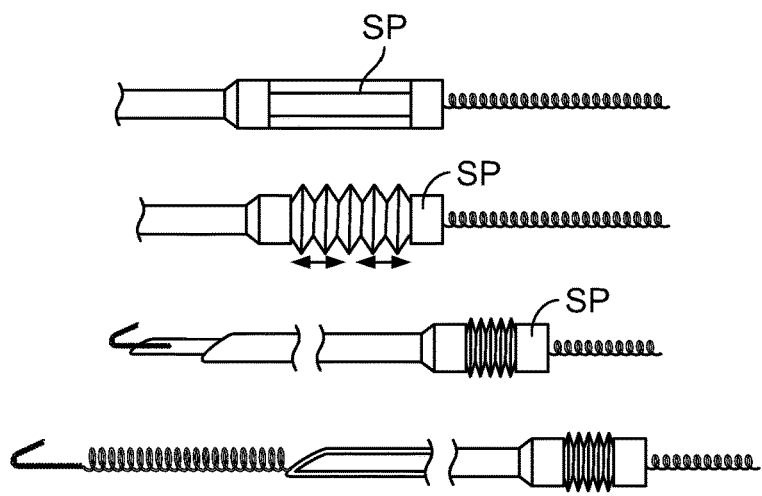
Figure 16A:
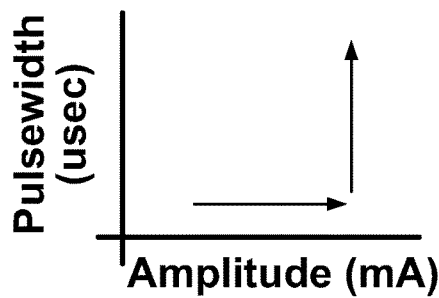
Figure 16B:
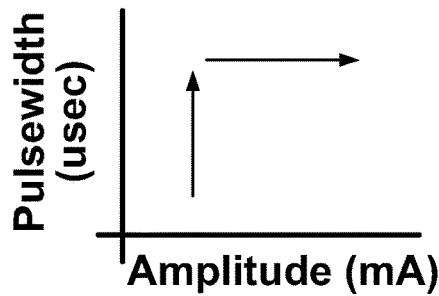
Figure 16C:
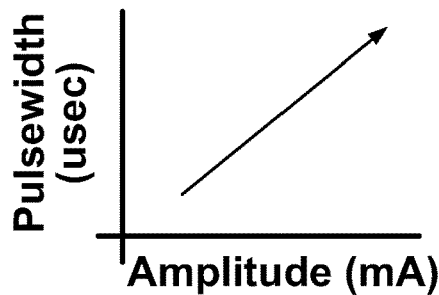
Figure 17:
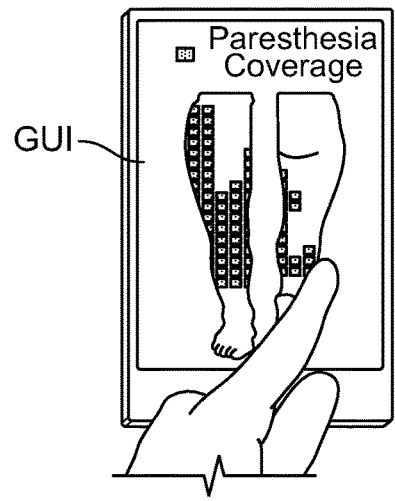
Figure 18A:
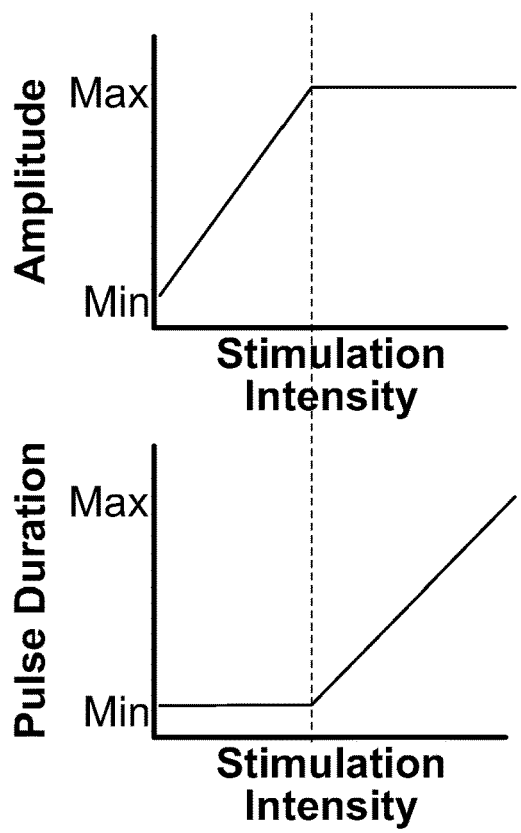
Figure 18B:
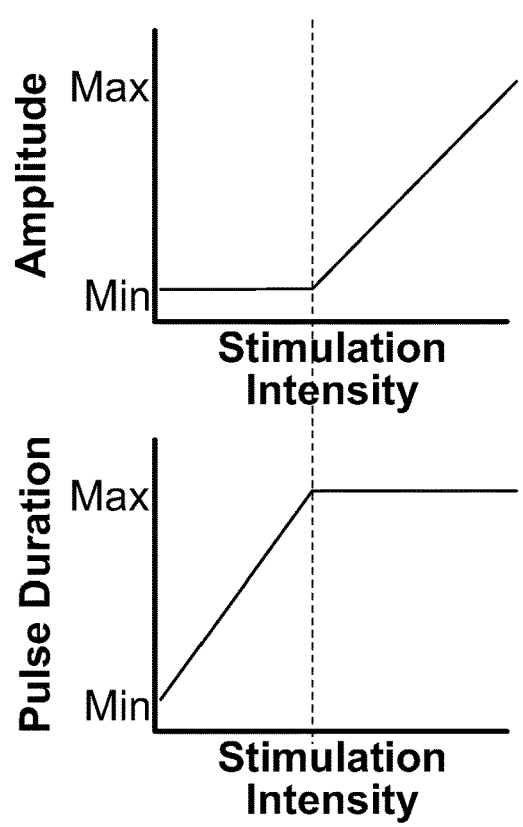
Figure 19:
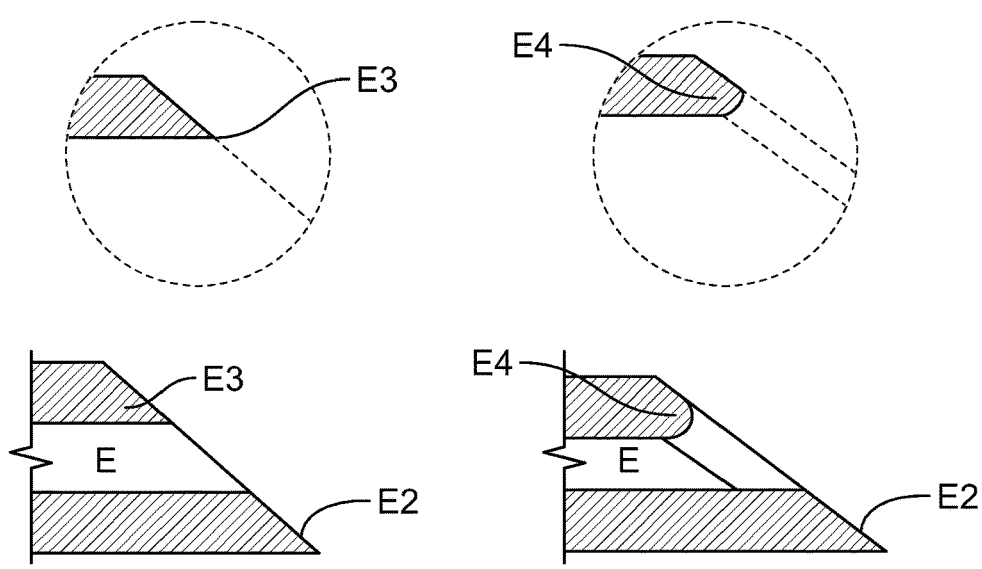
Figure 20A:
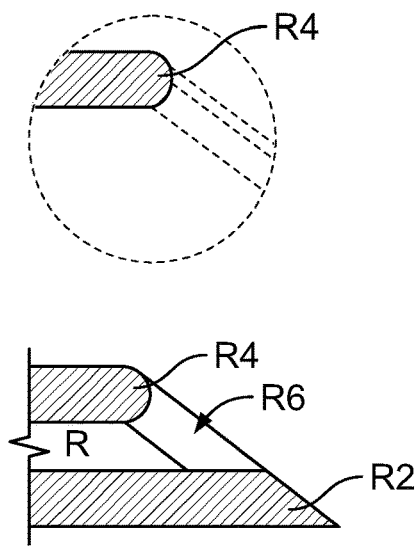
Figure 20B:
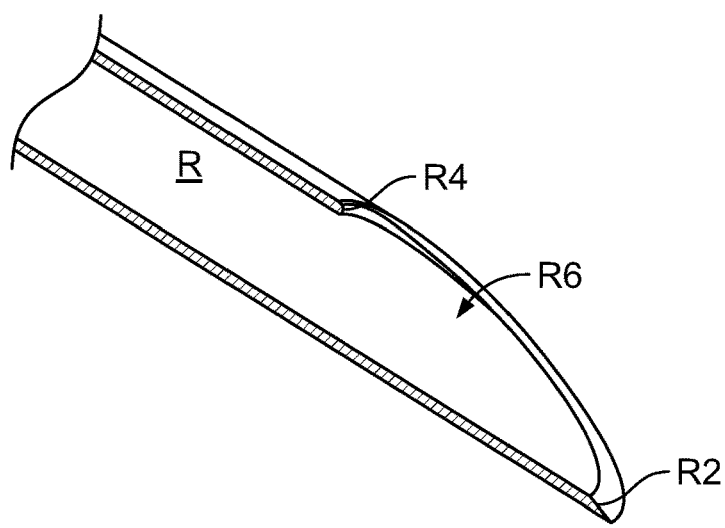
Figure 20C:
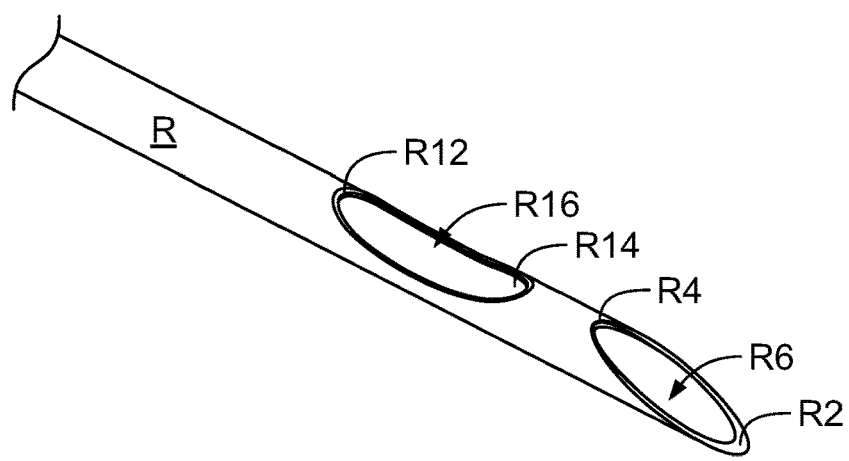
Figure 23:
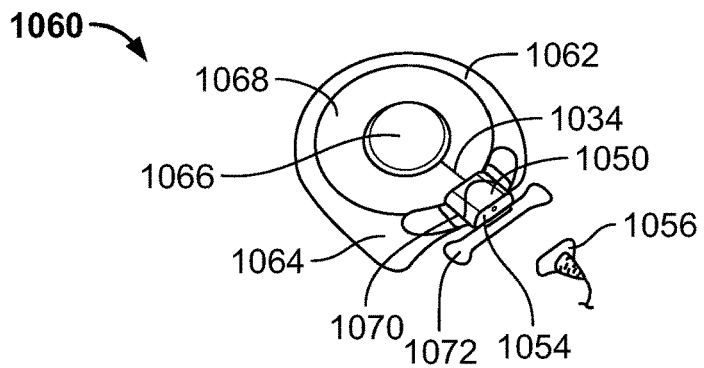
Figure 24A:
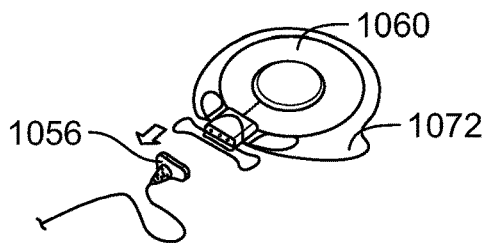
Figure 24B:
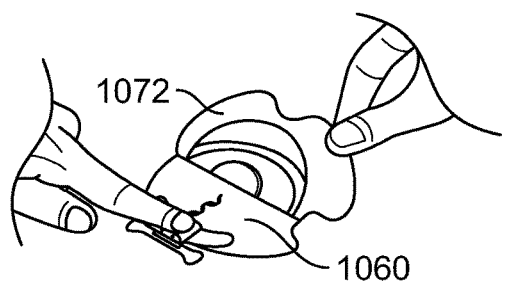
Figure 24C:
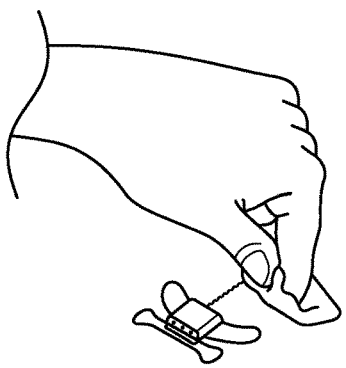
Figure 24D:
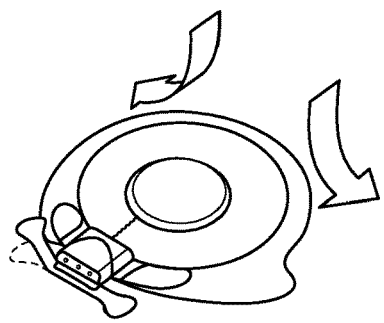
Figure 24E:
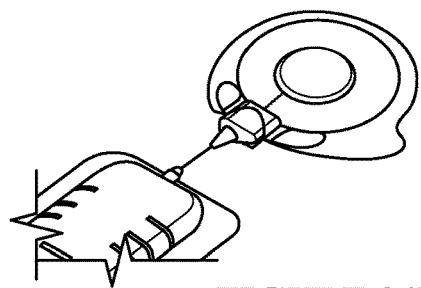
Figure 24F:
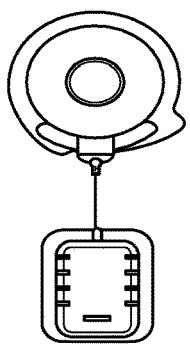
Figure 25A:
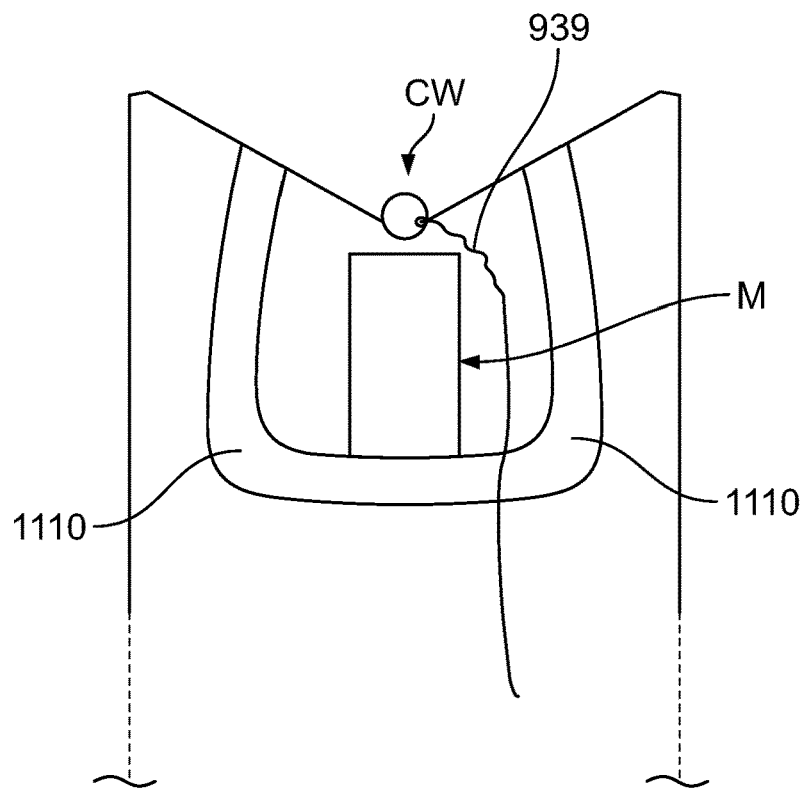
Figure 25B:
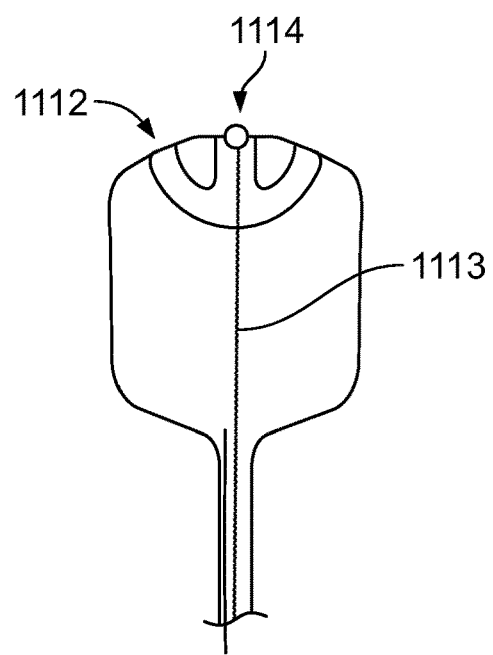
Figure 25C:
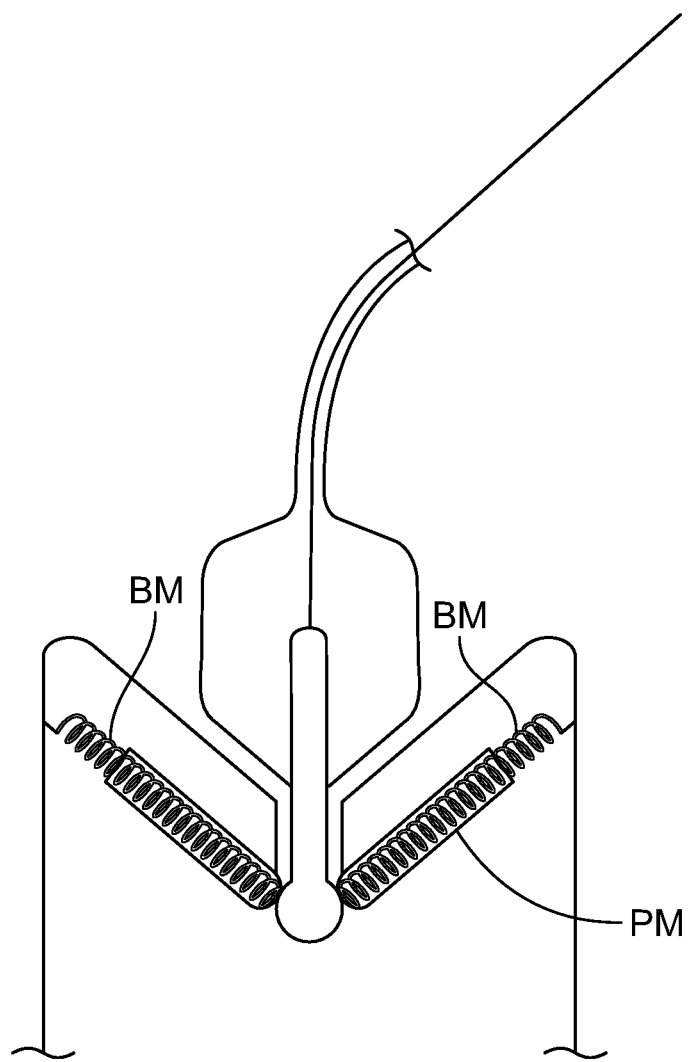

system with an inner sheath having a first bevel level and an outer sheath having a second bevel level, in accordance with described aspects;

FIG. 4 is a cross-sectional view of an introducing system with an outer sheath having a grooved formed in an inner surface, in accordance with described aspects;

FIG. 5 is a perspective view of an introducing system with an inner sheath and an outer sheath in a window configuration, in accordance with described aspects;

FIGS. 6, 7A, and 8 are views of an introducing system showing alternative delivery mechanisms, in accordance with described aspects;

FIG. 9A is a perspective view of various bevels of sheaths, in accordance with described aspects;

FIG. 9B are perspective and cross sectional views of modifications to the outer sheath that minimize the overall profile of the needle/distal electrode combination, in accordance with described aspects;

FIG. 9C are perspective views of embodiments in which the distal section of the electrode is secured to the sheath in accordance with described aspects;

FIG. 9D are top and cross sectional side views of embodiments in which the distal section of the electrode is secured to the sheath in accordance with described aspects;

FIG. 10 is a perspective view of an introducing system within an inclined member of an inner sheath, in accordance with described aspects;

FIG. 11 is a perspective view of a proximal end of an outer sheath of an introducing system, in accordance with described aspects;

FIGS. 12A and 12B are perspective views of certain embodiments of the connection between the lead and the lead connector in accordance with described aspects;

FIG. 13 is a perspective view of certain embodiments of the introducer system's ergonomic features in accordance with described aspects;

FIGS. 14A through 14E are views of certain embodiments for the delivery mechanism in accordance with described aspects;

FIGS. 15A and 15B illustrate spacer mechanisms in accordance with described aspects;

FIGS. 16A through 16C illustrate exemplary stimulation patterns useful in accordance with described aspects;

FIG. 17 depicts a type of graphical user interface that may be included in accordance with described aspects;

FIGS. 18A and 18B illustrate ways in which stimulation intensity may be adjusted in accordance with described aspects;

FIG. 19 is a cross sectional side view of two separate prior art needles;

FIG. 20A is a cross sectional side view, FIG. 20B a partial cut-away perspective view, and FIG. 20C a full perspective view of needle having fully rounded facings to accommodate an electrode in accordance with described aspects;

FIGS. 21A and 21B depict exemplary embodiments of the insulation displacement connector in accordance with described aspects;

FIGS. 22A through 22D illustrate various arrangements for the quick disconnect features contemplated in accordance with described aspects;

FIG. 23 is a perspective view of the bandage system in accordance with described aspects;

FIGS. 24A through 24F illustrate how the bandage system may be applied or replaced in accordance with described aspects; and FIGS. 25A through 25C are schematic representations of quick disconnect features contemplated in accordance with described aspects.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination. As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Described herein are systems, apparatuses, and methods that may conveniently provide and/or facilitate a single deployment device to incorporate implantation of a lead. The lead (also referred to as a micro-lead, fine-wire lead or simply electrode) may possess a generally small diameter in comparison to previous systems, with optimal sizes of less than 1.0 mm and, more preferably, less than 0.6 mm. Further, the electrode may have a generally coiled or helical structure, rather than a smooth cylinder. However, the present teachings are not limited to this structure of lead. Any appropriate configuration may be utilized without departing from the present teachings. In an aspect, embodiments described herein may conveniently provide a single device that may locate a desired tissue region, test stimulation of the tissue region, position (or reposition) a testing signal, and/or deploy an electrode or lead. The example embodiments may enable repositioning of the device and lead within human or animal tissue without deploying the electrode or lead until its deployment is desired by the user (e.g., the clinician). Embodiments may provide an easy to use and safe systems, apparatuses, and/or methods.

For the sake of clarity, the term "proximal" in the context of this application typically refers to the end of the electrode that is not inserted into the body and "distal" typically refers to the electrode end that is inserted into the body near the nerves. Depending upon the manufacture of the electrode structure, this proximal end may be wrapped in an insulating or protective coating or wrap. To the extent electrical connections must be made with the proximal end, the components at issue will allow for the removal of such coating(s)/wrap(s). The coating/wrap may include markings to serve as indicia of mobility that help to gauge whether the electrode has been repositioned or dislodged during system use, and particularly when outside of the oversight of a clinician.

As used herein, the terms inner sheath, introducer, introducing needle, inner needle, inner probe, introducing member, and/or the like are utilized interchangeably unless context suggests otherwise or warrants a particular distinction among such terms. The terms outer sheath, delivery needle, outer needle, outer probe, outer member, and/or the like are utilized interchangeably unless context suggests otherwise or warrants a particular distinction among such terms.

The introducing device may enable a lead to be percutaneously placed a safe distance from a surgical site, which may increase safety, minimize risk to the anatomy that is the focus of the surgery, minimize the risk of infection, and minimize the potential impact of any infection should it occur. As a non-limiting example, the device may enable placement of the lead to deliver stimulation to a nerve innervating a region, where the region may be painful or be anticipated to be painful due to a surgery (e.g., the device may enable placement of a lead to deliver stimulation to a femoral nerve, sciatic nerve, or lumbar plexus innervating a region, such as a knee which may be undergoing knee replacement surgery), and the device desirably enables the lead to be placed a safe distance (e.g., in the upper thigh, upper leg, or lower back) away from the surgical site (e.g., the knee) and/or outside of the surgical field.

The introducing device may enable a target nerve to be identified prior to lead placement and prior to lead deployment as part of a non-surgical procedure.

There is a clinical need for a device that delivers therapeutic electrical stimulation (e.g. peripheral nerve stimulation (PNS)) to a nerve (e.g. peripheral nerve) innervating the region of pain to provide pain relief. The device may deliver stimulation to the nerve transmitting the pain signal or it may deliver stimulation to a nerve, which is not transmitting the pain signal, but when stimulation is delivered, a condition or symptom, such as pain, may be relieved or improved and/or function may be improved or restored. The device may deliver pain-relieving or function-restoring peripheral nerve stimulation in a variety of settings including chronic, acute, post-surgical, post-traumatic, and intermittent pain and/or loss of function, and other conditions (e.g., other types of pain and/or functional loss), as well as across a range of anatomical regions, including but not limited to limbs (e.g., arms, legs, etc.), extremities (e.g., hands, feet, fingers, toes, etc.), joints (e.g., hips, knees, shoulders, elbows, ankles, wrists, etc.), back, neck, head, face, and other regions.

The device may enable the delivery of electrical stimulation to provide pain relief or functional improvement immediately following surgery. The device may also improve function, strength, and range of motion following surgery, as well as accelerate post-op recovery. The device may enable delivery of stimulation before, during, and after surgery, as well as in scenarios not involving surgery, such as acute or chronic conditions within or outside of the context of surgery.

Additional embodiments of a percutaneous stimulation system according to the present teachings are described below. In the descriptions, all of the details and components may not be fully described or shown. Rather, the main features or components are described and, in some instances, differences with the above-described embodiment may be pointed out. Moreover, it should be appreciated that these additional embodiments may include elements or components utilized in the above-described embodiment although not shown or described. Thus, the descriptions of these additional embodiments are merely exemplary and not all-inclusive nor exclusive. Moreover, it should be appreciated that the features, components, elements and functionalities of the various embodiments may be combined or altered to achieve a desired percutaneous stimulation system without departing from the spirit and scope of the present invention.

The described invention can reduce lead placement and testing procedure duration when placing one or more self-anchoring leads. Specifically, placement and testing times are reduced in comparison to prior art systems by reducing the number of percutaneous insertions required (e.g., the insertion of a needle for test stimulation and a separate needle for lead deployment or a system in which multiple percutaneous needles/tubes/catheters are inserted to increase the size of the percutaneous entrance and allow the lead to be inserted). Thus, in contrast to prior systems requiring multiple insertions and/or separate leads to deliver stimulation, the present system allows for greater manipulation of the introducer system, particularly along its axial length (i.e., the depth to which the needle is inserted and repositioned without deploying the lead anchor. Also, while some prior systems relied on a self-anchoring lead made from a flexible coil having a distal anchor electrically and mechanically integrated within the electrode, the present system marks a further improvements to the fracture-resistance of the flexible, helical coils by protecting them from stress and metal fatigue during the insertion procedure (in addition to the migration-resistant and infection-resistant qualities of such flexible coiled or helical structures).

A non-limiting example of the present system includes an introducing and testing system which reduces the number of percutaneous insertions required and/or enables the goals of introducing, testing, and/or lead deployment to be achieved with a minimal number of insertions (e.g., as few as one (a single) insertion). Specifically, the stimulation testing and lead insertion/deployment may all be incorporated into a system which may require as few as one (a single) percutaneous insertion, injection, or placement. The invention described here eliminates these issues while still allowing for a migration resistant coiled lead with a distal anchor to be deployed.

The introducing device may include an outer or delivery sheath. An inner sheath, stylet, or introducing member may be disposed within the outer sheath. The inner sheath is configured to engage and/or manipulate an implantable electrode. In an example, the delivery sheath may comprise a stimulation probe having an uninsulated portion at or near a distal end of the delivery sheath. The outer sheath may be coupled to a power source or stimulation signal generating circuitry at a proximal end. A clinician may control application of the stimulation signal to a tissue region via the outer sheath. The clinician may probe tissue regions to apply a stimulation signal and observe a response to the stimulation signal (e.g., a nerve response, a muscle response, etc.) or a lack of response. When the clinician observes a desired response at a target tissue region (e.g., region where desired response is observed), the clinician may facilitate deployment of an electrode. For instance, the clinician may press, twist, or otherwise manipulate a mechanical/hydraulic/electrical mechanism (or other appropriate mechanism) to cause the inner sheath and an electrode lead to translate with respect to the distal end of the outer sheath. When an anchor region (e.g., a terminal portion having a bend, barb, hook, etc.) of the electrode is at least partially deployed, the clinician may retract the inner sheath and/or outer sheath while the electrode remains in or near the desired tissue region. The anchor region may be uninsulated to allow for a stimulation signal to be delivered. In another aspect, the electrode may include a microlead or an insulated area that may extend from the anchor region and may connect to a stimulation source. It is noted that the stimulation source may be wearable, implantable, or various other appropriate types of stimulation sources, such as those disclosed in U.S. Patent Publication No. 20150073496 A1, which is incorporated by reference in its entirety.

Turning now to FIGS. 1 and 2A through 2D, one embodiment of lead introducing system 100 is shown, with particular emphasis on how the lead is deployed. While the same system is shown in each of these figures, certain reference elements have been omitted in certain views in an effort to highlight specific aspects of the view shown in that figure. The introducing device 100 includes an inner sheath 102, an implantable electrode 130, and an outer sheath 150. The outer sheath 150 may comprise a hollow tube or needle having an outer sheath cavity 154. In an embodiment, the outer sheath 150 may be a 19-gauge needle with an inner diameter of approximately 0.5-1.0 mm and an outer diameter of approximately 0.8-1.20 mm. In one embodiment, the outer sheath 150 may have an inner diameter of approximately 0.85 mm and outer diameter of approximately 1.03 mm. Outer sheath 150 may be between approximately 100-150 mm in length. In an embodiment, the outer sheath 150 may have a length of approximately 125 mm.

The outer sheath 150 may be constructed from an echogenic, i.e., highly visible under ultrasound conditions, material to facilitate use of the system 100. Such materials include, but are not necessarily limited to, a polymer, metal, stainless steel, or a combination of two or more materials. Additionally or alternatively, the shape of the outer sheath itself may be constructed so as to be effectively echogenic. Still further, only certain portions of the introducer system, including but not necessarily limited to the outer sheath, could have echogenic features (either by way of materials or construction/shape).

The inner sheath 102 is disposed within the outer sheath 150 so as to allow it to protrude from the cavity 154, as shown and described in FIGS. 2A-2D below. The inner sheath comprises an inner sheath cavity 104. In an embodiment, the inner sheath 102 may be a 21-gauge needle with an inner diameter of approximately 0.5-0.9 mm and an outer diameter of approximately 0.7-1.10 mm. In one embodiment, the inner sheath 102 may have an inner diameter of approximately 0.61 mm and outer diameter of approximately 0.8 mm.

The inner sheath 102 comprises any appropriate material including, but not limited to, any appropriate material, including, but not limited to, a polymer, metal, stainless steel, or a combination of two or more materials. The implantable electrode 130 is at least partially disposed within the cavity 104, as well as along a portion of the interior of the inner sheath 102 so as to allow the electrode 130 to move freely relative to this interior surface. In an alternative embodiment described in more detail below, the electrode 130 has a coiled structure with a centrally disposed axial void space that may receive a stylet that serves as a deployment mechanism and/or structure support prior to deployment of electrode 130. In this alternative embodiment, the stylet engages the electrode along its axial void but once again allows for the independent movement of the stylet relative to the electrode under certain conditions.

Implantable electrode 130 may comprise a microlead 138 disposed within at least the interior of outer sheath 150. The electrode 130 itself is deployed through the cavity 104. The microlead 138 may extend from a distal lead anchor 134 and couples to (e.g., removably or irremovably) a stimulation signal generator (not shown). The lead anchor 134 may comprise an uninsulated portion of the electrode 130 that may be bent, hooked, barbed, or the like. As such, lead anchor 134 may deliver stimulation signals both during and after it has been positioned and deployed. Further, the electrode 130—including the lead 138 and anchor 134—may have any combination of the following on part or all of the components: a monopolar nature; a helical and/or open-coiled structure with a central void that could receive a stylet; and/or multiple strands of an electrically conductive material wound together and electrically in parallel relative to one another.

While the particular disclosure of implantable electrode 130 contemplates a subcomponent including a microlead 138 and anchor 134, the more general term "lead" can refer to the stimulation apparatus from its distal anchor all the way to its proximal connection to a stimulus generating unit, including portions that may be jacketed, covered, or coated by insulating material. In contrast, the general term "electrode" may refer to the exposed, electrically conductive portion of the lead that is inserted into the body to deliver stimulation.

Figure 1:
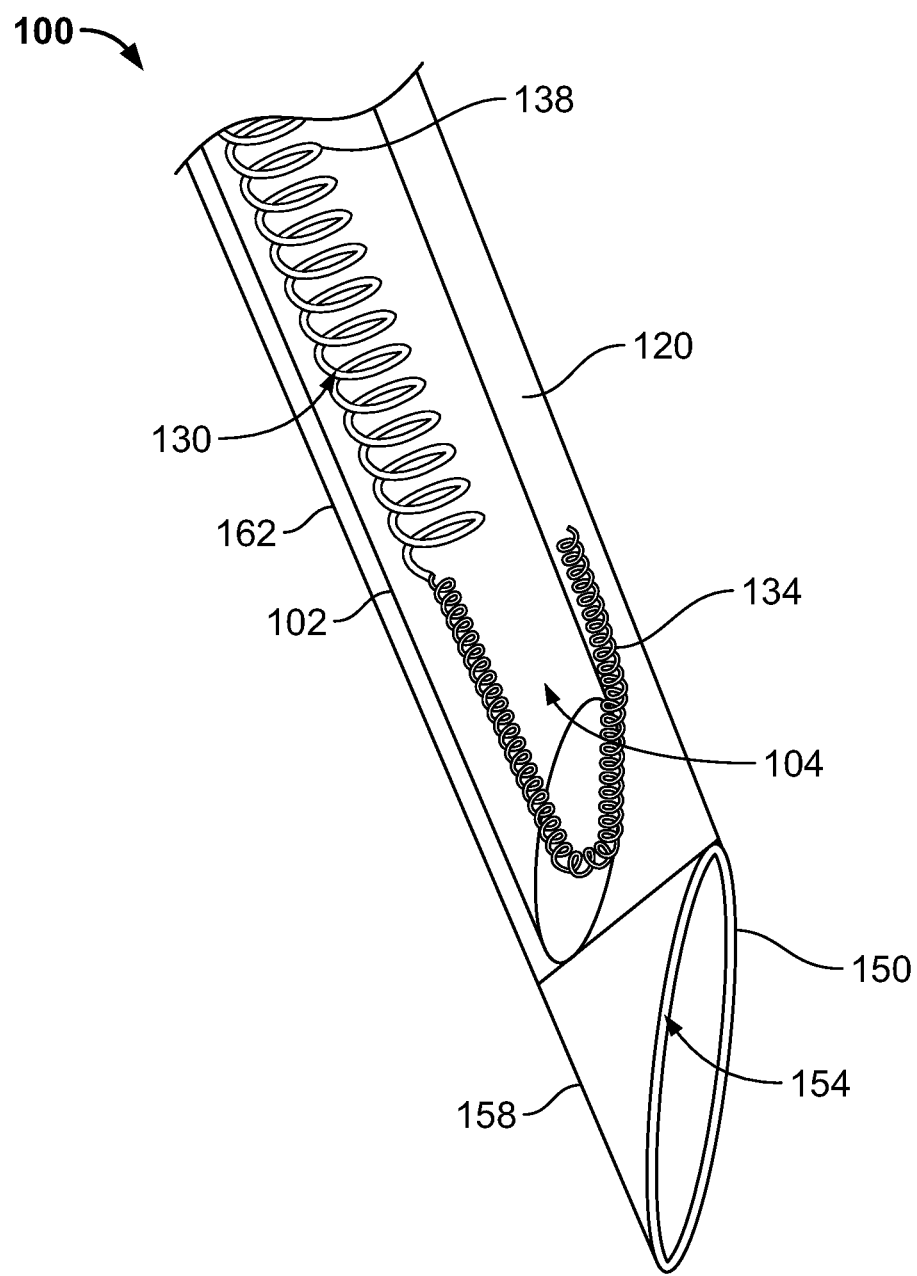
FIG. 1 is a partial, cross-sectional view of an introducing system with an un-deployed lead, in accordance with described aspects.
Figure 2A:
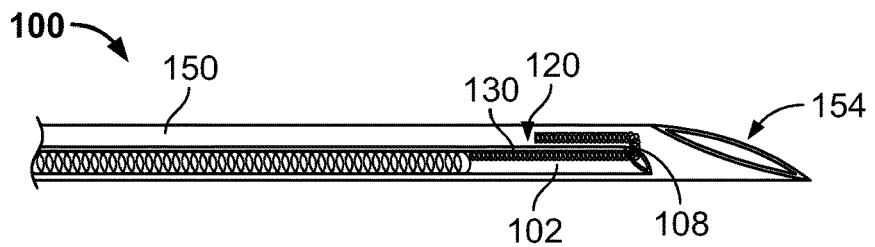
FIGS. 2A through 2D are partial, cross-sectional views of an introducing system as the lead is being deployed, in accordance with described aspects, while FIG. 2E includes partial cross-sectional views of an introducing system as the lead is being deployed along orthogonal axes (i.e., side view, front view, and—with respect to the first set of images—top view)
Figure 2B:
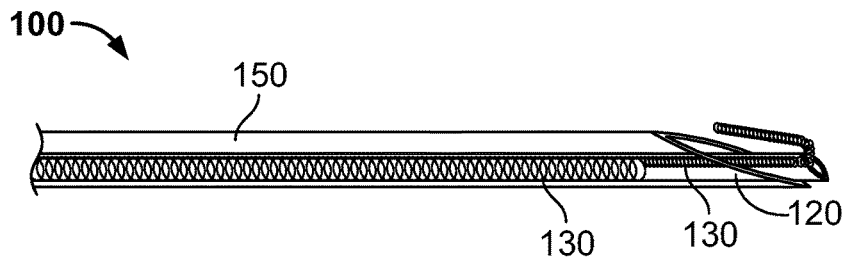
Figure 2C:
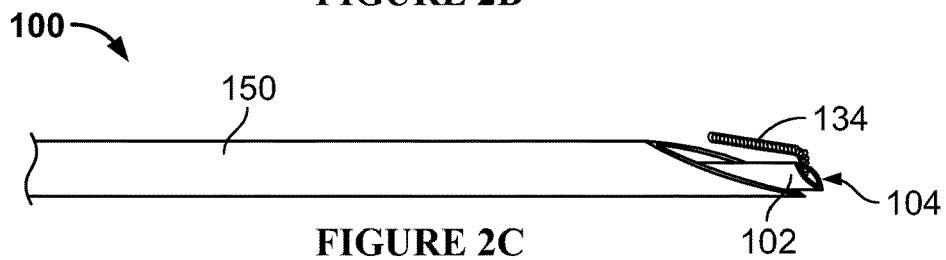
Figure 2D:
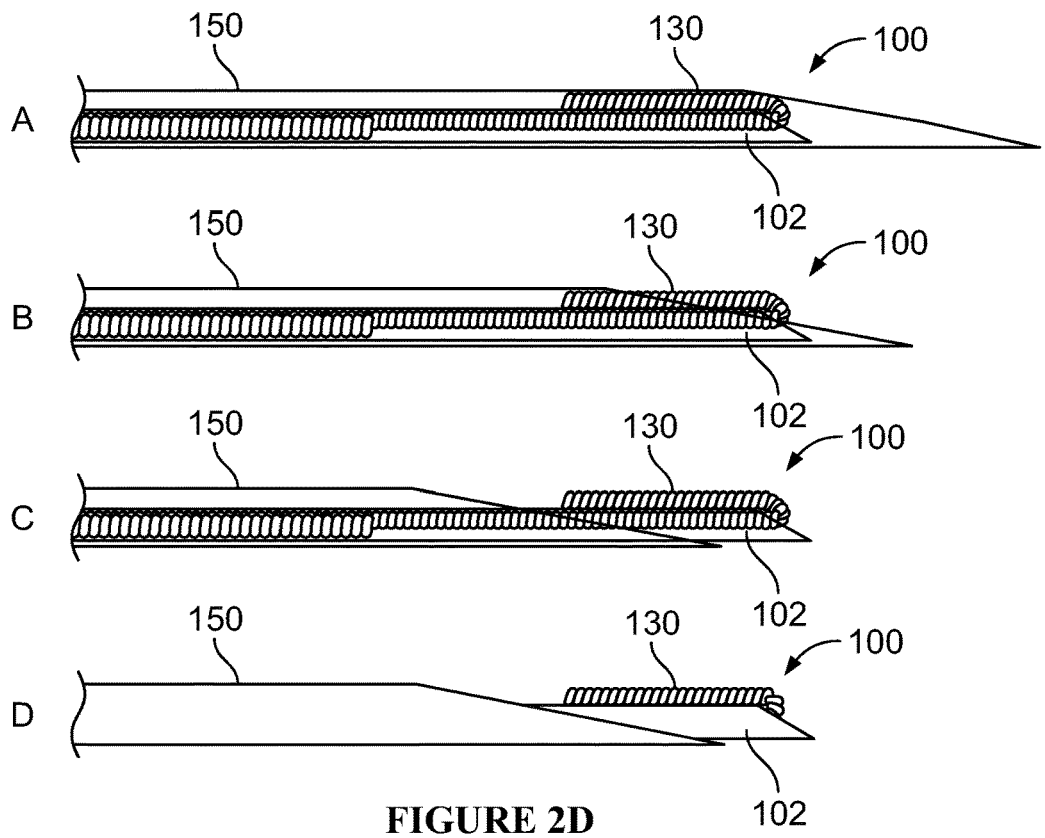

As shown in FIGS. 1 and 2A, the lead anchor 134 may comprise a bent or hooked portion such that a portion of the lead anchor may wrap around or hook around a distal end 108 of the inner sheath 102. When the lead anchor 134 is not deployed, a portion of the lead anchor 134 may be disposed in an area 120 between the inner sheath 102 and the outer sheath 150. The lead anchor 134 may be comprised of any appropriate material, including, but not limited to a polymer, a metal, stainless steel, or a combination or two or more thereof. An one aspect, the lead anchor 134 may be electrically and mechanically integral with the electrode through which stimulation is delivered.

Figure 2E:
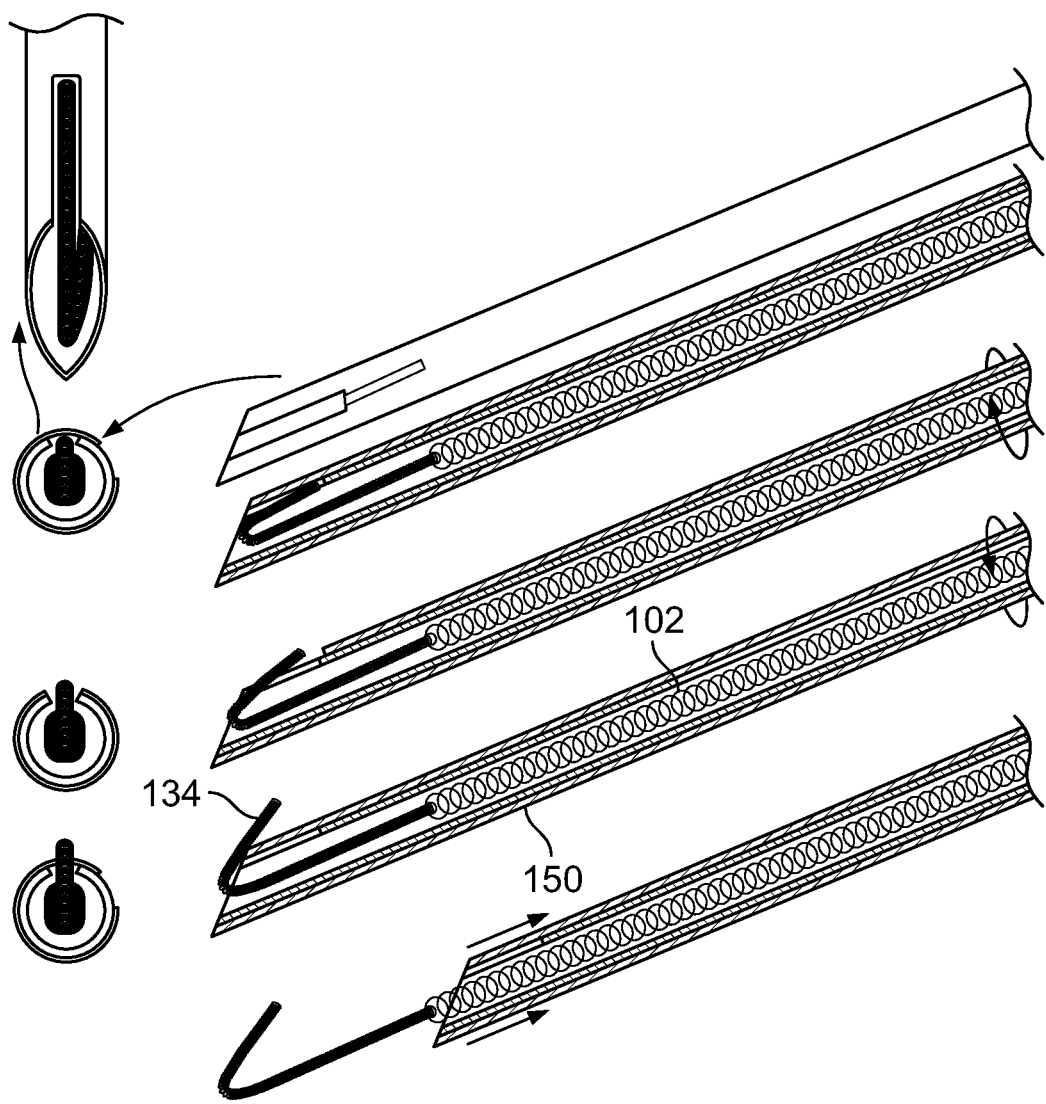

FIGS. 2A through 2C and 2D illustrate the relative movement of the inner sheath 102 and outer sheath 150. Upon insertion (FIG. 2A and inset (A) of FIG. 2D), these elements move in concert with one another. To deploy the electrode 130, the relative movement of one of the sheaths is apprehended or reversed, causing the electrode to protrude out of cavity 154. Once the inner sheath 102 is extended far enough out of cavity 154 (FIG. 2C and inset (D) of FIG. 2D), the distal anchor 134 is released from area 120 and embeds itself in the tissue proximate to the introducer system 100. The inner and outer sheaths are retracted (together or separately), and the electrode is released therefrom (e.g., temporarily disconnecting the electrode from the pulse generator to slide the sheaths off, physically removing the sheaths, etc.). As seen in FIG. 2E and as will be described in greater detail below, the deployment may also involve rotational movement (indicated by the arrows) that allows the anchor to be released and to protrude through a channel or slit of the sheaths.

The outer sheath 150 has an inner diameter that is sufficiently larger than an outer diameter of the inner sheath 102 so as to create the area 120 where a portion of the lead anchor 134 is disposed prior to deployment of the electrode 130. A distal end 158 of the outer sheath 150 may be uninsulated while a body 162 of the outer sheath 150 may be insulated, so as to allow current to be delivered to the distal end 158 while the body 162 of the outer sheath 150 does not directly stimulate tissue. It is noted that the area of the uninsulated distal end 158 may be about equal to an area of the uninsulated portion of the lead anchor (e.g., the electrode) 134 to ensure equivalent testing of stimulation on a target tissue region.

The present invention includes a lead insertion/deployment system and test stimulation system may be combined into a single system wherein electrode(s) (incorporated into the needle) are utilized for the delivery of test stimulation currents. In various non-limiting examples, the external portion of the system is insulated or non-conductive except for one or more portion that is un-insulated and conductive to serve as a stimulating test electrode contact. The stimulating test electrode contact may be mechanically integrated with the outer needle with the electrode contact located appropriately, such as at a location which provides information to guide correct/optimal positioning of the lead prior to its deployment.

The characteristics of the electrode contact may be designed to represent, predict, or otherwise provide information regarding the performance of the lead prior to lead deployment, particularly with respect to size, shape, material, and surface area. For example, by selecting mechanical and/or electrical properties similar to or representative of the lead electrode contact (e.g., similar impedance, contact materials such as stainless steel, and/or similar surface area such as 10 $mm^2$)), the characteristics of the test electrode contact will represent the anticipated performance of the lead. The test electrode position should be at or near the distal end (or tip) of the introducer needle such that, when the self-anchoring lead is deployed, the lead remains in close proximity to the location occupied by the test stimulation electrode. Alternatively, multiple electrode contacts may be advantageously spaced along the needle/sheath (e.g., 1 mm-30 mm intervals, preferably 1 mm) such that test stimulation can be delivered from one or more different test electrode contacts on the same needle, thereby allowing the optimal location for stimulation to be identified while minimizing or eliminating the need to move and reposition the lead introducing system during the test stimulation/optimal location identification procedure. In such multiple test electrode configurations, test stimulation is delivered from multiple locations from one percutaneous insertion to determine the optimal deployment location for a self-anchoring, infection and migration resistant coiled lead with a distal anchor/electrode.

In an embodiment, the lead anchor 134 may fold over the inner sheath 102, e.g., at the distal end 108 of the inner sheath 102, so the lead anchor 134 may be contained in the area 120 between the inner sheath 102 and the outer sheath 150 prior to deployment of the lead anchor, e.g., during testing and/or the locating a target tissue region. This containment of the lead anchor 134 may allow for testing of tissue stimulation and reposition of a location of delivery prior to deployment of the lead anchor 134, among other potential uses.

Test stimulation used for lead deployment may be accomplished by passing electrical current into the surrounding tissue through the needles and/or sheaths or test electrode(s) situated on an exterior surface(s) thereof. The test electrodes could be formed via openings in an insulating polymeric jacket situated around the outer sheath 150 (or, in some embodiments, the inner sheath 102) with current passing through the sheath itself for stimulation, or the electrodes could be discretely formed elements (possibly including discrete wiring for stimulation signals). Other arrangements contemplate the use of a conductive coating (making appropriate contact with a pulse generator/signal source) disposed along selected exterior surfaces of one or both sheaths. Alternatively, test stimulation can be accomplished through an exposed portion of the electrode 130 itself. In this arrangement, a portion of the distal end of the lead protrudes through cavity 154 (and, in some embodiments, cavity 104), while the lead itself remains in a non-deployed state (i.e., in some embodiments, the anchor portion 134 is still held firmly within area 120). In either instance, after insertion of the introducer device 100 into the tissue, test stimulation is delivered prior to the deployment and anchoring of the lead in that tissue.

Figure 3A:
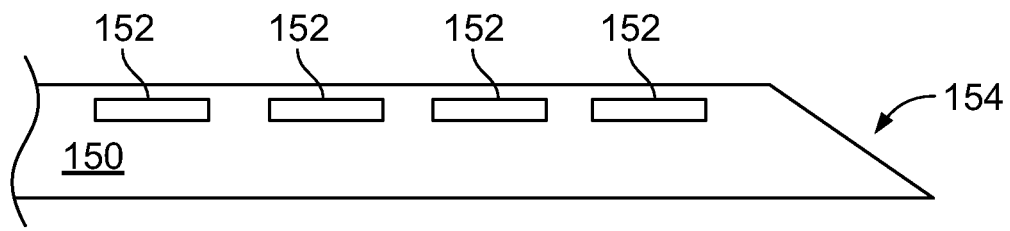
FIGS. 3A and 3B are cross sectional side views of an introducing needle having multiple test electrodes positioned around the exterior surface of the outer sheath.
Figure 3B:
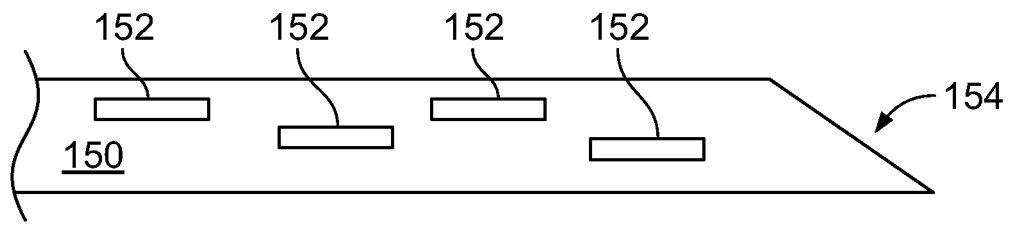

In FIGS. 3A and 3B, the exposed exterior portion or portions of the needle 150 include multiple test electrodes 152. Test electrodes 152 may be positioned at intervals along the length of the needle and/or radially at different locations around the circumference of the needle. While some embodiments may include only a single test electrode, the use of multiple electrodes is advantageous because it enables test stimulation at multiple locations in the tissue with as few as possible (e.g., single) insertions and/or injections and/or movements of the needle, ensuring the procedure is simple and time efficient, while avoiding the need to reposition the introducer or lead to evaluate other potential electrode locations. While the outer sheath 150 is depicted, the inner sheath (if used) may incorporate similar test electrodes. In this arrangement, it will be understood that the inner sheath must be sufficiently expelled through the cavity 154 in order to expose the test electrodes 152 to tissue intended for test stimulation, although in this arrangement the inner sheath should not be expelled so far outside of the outer sheath as to cause the anchoring system 134 to become embedded in the tissue. Electrodes 152 may be positioned in regular or irregular intervals, along a straight linear line or around portions or the entirety of the circumference of the needle. Although multiple electrodes are shown, some embodiments may require only a single test electrode. Also, while the electrodes are depicting as running along the length of the needle, it may be possible to position the electrodes at different positions around the circumference, or even to use a fully circumferential electrode at one or more locations.

In another embodiment, the electrode (e.g., the simulated electrode surrounded by insulative material or the conducive electrode on the surface of the needle and/or sheath) may be repositionable (e.g., through a pulling or twisting control mechanism in the needle hub or handle) and may be used to test stimulation in multiple locations, offering the advantage that multiple locations of test stimulation may be applied in a single insertion without deploying the lead. In another embodiment, a coating (e.g., insulative, polymeric) may be partially or completely applied to any surfaces (e.g., conductive, metallic) in contact with the lead and/or the external needle (e.g., interior of inner needle or outer needle, exterior of inner needle), so as to prevent current discharge from undesired locations and enabling proper stimulation for use to identify locations for lead deployment.

In all embodiments, a lubricious coating (e.g., a hydrophobic coating such as polytetrafluoroethylene) and/or a biocompatible lubricant (e.g., a silicon based material) lubricant be applied along any portion of the needle and/or along other moving parts within the system 100 to improve ease of manipulation of the introducer components (e.g., the sheaths and/or needles) as directed by the clinician. This arrangement enables ease of movement and helps to avoid the need for larger diameters in the introducer in the design, as well as minimizing the risk of improper movement of the needles which may damage the lead and improving the simplicity of the lead placement procedure to eliminate the occurrence of technical difficulties for the clinician.

Figure 3C:
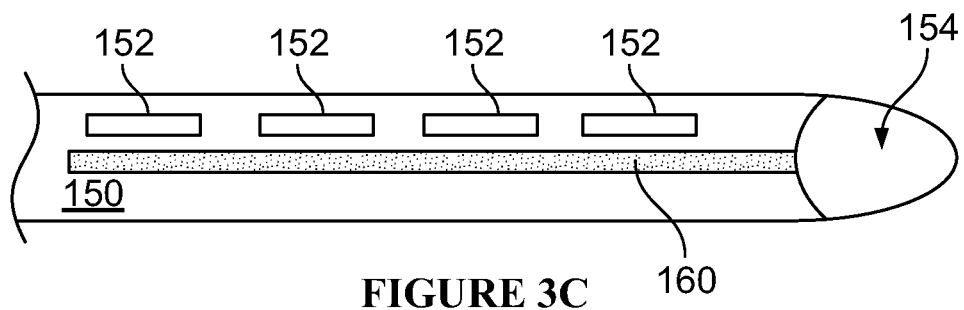
FIG. 3C is a combination of side and axial cross sectional views of an introducing needle having a series of slits to provide for test stimulation by the electrode itself.

In FIG. 3C (which is rotated in comparison to the views shown in FIGS. 2A through 3B so as to eliminate a view of the edge of the distal end of the needle), a slit 160 is provided along a length of the outer needle 150. While shown as running all the way to the tip 154 of the sheath 150 along its underside, it will be understood that the channel 160 may be formed in a line or pattern along only a portion of the sheath 150 or, it may include a series of slits, channels, or apertures to accommodate the lead anchor (not shown in FIG. 3C) as described herein. Further, the channel, slits, or apertures may be formed along any axis of the sheath, rather than being limited to only the top or underside. Optional test electrodes 152 may also be positioned proximate to the slit facilitate positioning of the introducer system. After appropriate test stimulation and positioning, the electrode is rotated relative to the outer sheath 150 so as to allow the anchor (not shown) to release and deploy into the tissue. The clinician will ensure that this deployment corresponds to the optimal test electrode(s) 152 as identified during the test stimulation procedure.

In an aspect, the introducing device 100 may be designed to incorporate two needles with a minimal size increase over a one needle design, for example. As shown in FIG. 4, the outer sheath 150 may have a groove 156 along at least a portion of its inner surface 158, forming a space for the lead anchor (not shown in FIG. 4). This design may allow the lead anchor 134 to fit and/or translate into the groove 156. In an aspect, the groove 156 may allow for a smaller diameter of the outer sheath 150 as additional room, e.g., area 120, for the lead anchor 134 is reduced.

In an embodiment as shown in FIG. 5, the diameter of the sheaths may be reduced by having a slot 110 on the inner sheath 102, such that the lead anchor 134 can re-enter the inner sheath 102 after its deployment, thereby allowing the outer sheath 150 to be situated close to, or even in direct contact with the inner sheath 102. The distal end 108 of the inner sheath 102 comprising the slot 110 and the lead anchor 134 that extends beyond the inner sheath 102 and re-enters into the slot 110 may be situated external to the outer sheath 150, so that the remainder of the inner sheath 150 may remain in direct contact or nearly direct contact with the outer sheath 150. Further, the inner sheath 102 may be comprised of any appropriate material, including, but not limited to, thin-walled polymers, metals, stainless steel, or a combination thereof. A thinner material for the inner sheath 102 may allow the outer sheath 150 to have a smaller diameter and still contain the inner sheath 102 or a portion thereof.

Applying test stimulation (e.g., stimulation performed prior to or during lead deployment and/or repositioning) that is representative of stimulation by the lead itself is advantageous because it allows clinicians to quickly and simply identify the desired location for lead deployment through a minimal number of needle insertions, avoiding the need to reposition the needle(s) and/or lead. Minimizing needle insertions minimizes the risks and discomfort for the patient and, generally, provides a more reliable method for lead deployment in comparison to previous systems.

Although shown as having a tapered edge that is similar to that of outer sheath 150, the distal end of the inner sheath 102 does not have to be a cylinder; rather it may be any appropriate size and shape. For example, the distal end 108 may be beveled, cylindrical, partially-cylindrical, notched, rectangular, or the like.

In an embodiment as shown in FIG. 6, the functions of the inner sheath 602 may be embodied/replaced by a shaft with a curved arm or end portion 656. The curved end can be locked across the inner sheath cavity 504 to hold the bent anchor of the lead 634. When ready for deployment, the inner sheath 602 may be pushed forward, engaging the anchor 634 to position or otherwise dispose the anchor 634 in the tissue. The inner sheath 602 can be rotated to the side and withdrawn into the inner sheath cavity 504. The curved arm 656 may then rest along the inner wall of the inner sheath 602 or may be otherwise positioned to allow the inner sheath 602 to be withdrawn while leaving the deployed anchor 634 in place.

The lead insertion/deployment and test stimulation systems may be combined into a single system in which a lead deployment mechanism is contained within a single sheath/needle/tube which contains the lead. This example may consist of a stylet which runs through and/or alongside the lead within an introducing needle/sheath. As seen in FIG. 7, the stylet 170 may provide the flexible coiled lead with increased stiffness, allowing the lead to be manipulated within the needle. In this example, the anchor of the lead may be contained entirely within the introducing needle and/or be secured such that the system may be repositioned without deploying the anchor until such a time as deployment of the lead and anchor is desired. A release mechanism may engage the electrode/lead along one or any number of points, with a release mechanism accessible to the clinician to allow for selective retraction of the stylet 170 after the system 100 is positioned appropriately.

This stylet system solves the problem of selectively deploying a self-anchoring lead, creating a selectively self-anchoring lead deploying system with significant advantages over the prior art including a lead that has design advantages such as infection resistance, migration resistance, fracture resistance, selectively self-anchoring mechanism, an anchor which is integrated with the electrode contact(s) such that stimulation can be delivered through the anchor (further ensuring correct positioning of the contact is maintained as desired), a design and/or fabrication that enables the lead to remain in the desired location within the tissue while in use for therapy and/or trial/testing and then enable easy, safe, comfortable, and/or reliable withdrawal/removal when desired. Although the stylet or core may be used in an embodiment with a single sheath/needle/tube, it can also be utilized in combination with a system of multiple sheaths wherein one or more sheaths are used for housing/securing the lead and/or for delivering test stimulation and the stylet/core is used to position/deploy the self-anchoring lead in the optimal location. Non-limiting examples of methods for lead and/or anchor deployment are described in other sections.

In another embodiment the lead and/or electrode anchor may be held in place (e.g., within one of the needles and/or sheaths) by a balloon (e.g., an inflatable and/or deflatable or expandable and/or compressible substance or device), whereby manipulation (e.g., inflation, deflation, compression) enables the lead to be released, exposed, and/or deployed (e.g., exposure of lead anchor, release of outer sheath needle enabling it to be withdrawn and the lead deployed). The use of a balloon is advantageous because it prevents premature movement of the lead, sheath and/or needle, stabilizes the lead and/or anchor to protect the lead or tip from damage, and can enable full deployment of the electrode lead anchor (e.g., into surrounding tissue) to secure the lead and prevent movement of the lead (e.g., following deployment or during retraction of the needle.

Further, as a non-limiting example, the uninsulated lead tip may be manufactured or bent in the shape of an anchor, but loaded into the needle and held in a straight position as seen in FIG. 8. In this case, the lead tip anchor 134 will be designed and manufactured to return to its original shape during lead deployment. When exposed by retraction of the external needle 150 or advancement with the inner sheath or stylet 170 (as indicated by the various arrows in FIG. 8), the lead tip may bend to anchor into nearby tissue.

A straight lead tip may also be pushed by a balloon or sheath or pulled by a hook into an anchored position (e.g., bent). In an alternative embodiment, the lead may be composed, coated, or framed by a shape memory alloy (e.g., nickel-titanium alloy) that returns to a desired shape upon exposure a change in temperature or to the heat of the human body. Lead fracture rate may also be reduced by eliminating the need for storage of the lead with a bent tip, which will eliminate excess forces placed on the lead tip anchor during storage and lead placement.

Once testing has identified the desired position for placement of the lead anchor 134, the inner sheath 102 may be pushed forward relative to the distal end 158 of the outer sheath 150. In an aspect, the inner sheath 102 may be pushed forward until the lead anchor 134 is exposed. The inner sheath 102 and outer sheath 150 may slide relative to each other to expose part or all of the lead anchor 134. In an embodiment, the lead anchor 134 may move approximately 0.1-0.3 mm from its original location. In an embodiment, the lead anchor 134 may move approximately 0.2 mm from its original location. In an aspect, the outer sheath 150 may be pulled back/retracted until the lead anchor 134 is exposed. This aspect for the lead anchor 134 to remain stationary through the placement process, i.e., at the same position relative to the target tissue (e.g., nerve or nerve fiber(s)) and the non-target tissue. Once the lead anchor 134 is exposed from the inner sheath 102 and/or the outer sheath 150, the microlead 138 may be deployed and/or anchored to the target tissue region. Further, the inner sheath 102 and outer sheath 150 may also slide to recover a lead anchor 134 and/or microlead 138, such as to reposition the lead closer to or father from a target tissue region, e.g., a nerve. In an embodiment, the lead 134 may be exposed without deploying. In an embodiment, the lead 134 may be initially exposed without deploying and then may be deployed at a later stage. In an embodiment, the lead 134 may be repositioned multiple times.

It can be clinically useful to limit the difference in location between the final lead deployment site and the test stimulation site such that the clinical results of stimulation with the final, deployed lead in place are substantially equivalent to the results of stimulation during test stimulation in the optimal location. In at least one embodiment, the distal end 158 of the outer sheath 150 may comprise a generally different bevel (e.g., a deeper bevel or greater angle of bevel) than that of the distal end 108 of the inner sheath 102. This may allow the lead anchor 134 to be deployed without pushing the inner sheath 102 beyond the end of the outer sheath 150. The bevels of the distal end 158 of the outer sheath 150 and the distal end 108 of the inner sheath 102 may be angled in directly or partially opposed directions. This particular arrangement may limit how far the inner sheath 102 must be manipulated (e.g., pushed, etc.) to allow for deployment of the lead anchor 134. In an embodiment, the outer sheath 150 bevel may be more shallow or at less of an angle as compared to the inner sheath 102 bevel.

FIG. 9A illustrates various beveled tips for either of the sheaths 102, 150. In an embodiment, a short bevel or true short bevel with a steeper angle may be used as the inner sheath 102 bevel with a standard bevel or a longer bevel (with more gradual, less steep angle) on the outer sheath 150 bevel. This can provide significant advantages, such as allowing less movement of the needles/tubes relative to each other during lead deployment and allowing test stimulation to effectively predict the results of stimulation with the final (e.g., deployed) lead which delivers stimulation through the distal self-anchoring component of the lead.

The present invention includes a system which combines test stimulation and lead insertion/deployment into a single system. A non-limiting example wherein the lead insertion/deployment system and test stimulation system may be combined into a single system is one in which a self-anchoring lead is utilized for the delivery of test stimulation currents prior to being selectively deployed in the optimal location identified by test stimulation. In this example, the self-anchoring lead consists of one or more anchors located on the distal portion of the lead which are also the active/electrode portions of the lead (e.g., the stimulation current is delivered through the anchoring portion of the lead), which enables test stimulation delivered through the lead (and therefore through the lead anchor) to be optimally similar to final stimulation when the self-anchoring lead is deployed, as the anchor which secures the position of the lead in the tissue is itself delivering the stimulation. This example may consist of the lead anchor/active electrode portion being secured relative to the insertion needle such that all or a portion of the non-insulated portion of the lead (e.g., the electrode/anchor through which current is delivered to the targeted tissue) is exposed to the stimulation target tissue. In this example, the anchor of the lead may be secured such that the system may be repositioned without deploying the anchor until such a time as deployment of the lead and anchor is desired.

In summary, the securing of the lead may be embodied by the following: a sheath which secures the extreme (i.e., distal) end of the anchor while leaving a portion of the lead (e.g., the bend of the anchor) exposed to the tissue; a wrap or sheath which secures the anchor of the lead and may be opened/broken to deploy the lead anchor; and/containing the end of the lead within the insertion needle with a portion of the anchor (e.g., the bend of the anchor) extended beyond the proximal side of the needle bevel. These examples provide a system for the delivery of test stimulation within the same system used for lead introduction/deployment, eliminating the need for separate systems while still allowing the lead to be positioned/re-positioned as necessary until final deployment. This embodiment may be usefully combined with other portions of the invention described here such that the goals of introducing, testing, and/or lead deployment can be achieved with a minimal number of insertions (e.g., as few as one (a single) insertion).

The introducing device may enable multiple or additional lead locations or potential lead locations to be tested and evaluated prior to deploying the lead. In an aspect, the introducing device may enable the introducer to be advanced, withdrawn, or otherwise repositioned (e.g., moved forward or backward or in other directions) without deploying the lead. The introducing device may enable a system and a method for advancing, withdrawing, or otherwise repositioning (e.g., in any 3-dimensional tissue volume) a selectively self-anchoring lead. A non-limiting example of a non-selectively self-anchoring lead (e.g., a lead that was self-anchoring but not selectively self-anchoring) may include a lead with a distal electrode that may be integrated mechanically and electrically with a distal anchoring mechanism.

In previous technology, non-selectively self-anchoring leads would commonly experience unwanted deployment withdrawal or repositioning of the introducer. That is, if non-selectively self-anchoring leads and introducer systems were advanced beyond the optimal location (e.g., undesirably advanced too far, too close to the target nerve or structure, etc.), the non-selectively self-anchoring leads would still deploy at a suboptimal location because the lead could self-anchor and self-deploy when the introducer was withdrawn. Previously, non-selective self-anchoring leads and delivery systems could not be retracted, withdrawn, or otherwise moved backward without lead deployment. The present introducing device allows for use selective self-anchoring leads and delivery systems, including the associated devices and technology.

The introducing device includes a selectively self-anchoring lead and insertion system that may locate an optimum location for a lead to be deployed. In this manner, the lead is deployed only when desired, and it may be easily and/or atraumatically withdrawn when desired (e.g., when pain relief or restoration of function is no longer needed).

The introducing device provides a redirectable or steerable introducer and lead system. Previous devices did not teach a technology that could be steered in one direction and then redirected and steered in another (i.e., different) direction without deploying a self-anchoring lead. The introducing device enables one to steer a selectively self-anchoring lead and introducer system in multiple directions and redirect the lead and introducer system without deploying the lead.

The introducing device may also enable and facilitate the use of imaging guidance, such as ultrasound-guidance and/or fluoroscopic guidance, during the lead placement, testing, and/or lead repositioning procedure. Visualization of the position, orientation, and/or trajectory of the introducer and/or lead is critical for successful lead placement by the clinician.

Manufacturing the introducer system, and particularly the outer sheath 150 and/or lead 130, to incorporate easily visualized/identified indicia simplifies the lead placement procedure, reduces risk for the patient, improves reliability of lead placement, and avoids improper or premature deployment of the self-anchoring lead. The tip of the lead and/or other sections or lengths of the lead may be manufactured (e.g., coated, labeled, textured, etc) with alternative materials that are easily detected under medical imaging, as this is important to improve ease of lead placement and detection of the device with imaging. As a non-limiting example, the lead tip or portions or segments of the lead may be textured to increase echogenicity, improving visualization under ultrasound. In another embodiment, the tightly coiled and twisted structure of the multi-stranded lead wire may be braided, coiled or woven at the tip to increase reflectivity and echogenicity. Further, texturizing smooth metal or the addition of a textured conductive coating would enable better detection under ultrasound while enabling electrical stimulation. In another embodiment, the lead tip may be textured to improve echogenicity, but coated with a conductive material that results in a smooth surface that reduces potential for tissue damage, patient discomfort and enables easier removal from tissue. Alternatively, in another non-limiting example, the needle or a length of the tip may be coated, textured or marked to improve visualization under ultrasound. Modifications to the tip to increase echogenicity that increase surface area may also reduce the electrode impedance of the needle tip, enabling selective stimulation of the desired neural targets. In another embodiment, the two introducer needles or sheaths may be labeled, coated or etched in banded pattern to mark length along the shaft. In such an embodiment, the bands or labels may be used to assist in deployment of the lead at the desired depth, used to guide movement of the needles or sheaths in relation to the other, and used to differentiate these and facilitate lead placement under ultrasound imaging. Further, the markings of the sheaths or needles could be used as a scale for distance and depth during lead placement procedures that is important for estimating distances e.g., the distance of a nearby target or non-target structure and depth of insertion. In another embodiment, the introducer needle(s) or sheath(s) may be composed of materials which to enable magnetization (e.g., ferritic stainless steel, or non-metallic magnet) for detection with advanced ultrasound needle localization systems.

The position, orientation, and/or trajectory of the introducer and/or lead is important for successful lead placement by the clinician, for example under x-ray imaging, such as fluoroscope, x-ray or CT. Modifications to the existing introducer system and/or lead through the addition of radiopaque markers can simplify the lead placement procedure, reduce risk for the patient, and improve reliability of lead placement, allowing visualization of lead placement and avoiding improper or premature deployment of the self-anchoring lead. Additionally, the lead tip or needle may be coated with a radiopaque or radiodense substance (e.g., barium, radiopaque polymer) to improve visualization under x-ray imaging (e.g., fluoroscopy, x-ray, CT). Radiodense metals, e.g., platinum, gold, tantalum, or for example, a radiopaque conductive polymer, may be applied to the lead tip permitting visualization under x-ray imaging, while still enabling current flow for stimulation. As a non-limiting example, a portion of the lead, including the uninsulated or insulated wire, may be coated or manufactured with a radiopaque material, such as with a titanium, tungsten, barium sulfate, and zirconium oxide, to enable better detection under fluoroscopy or x-ray. This will enable visualization on x-ray of potential fragments to enable better detection of lead fragments left behind after lead removal. In one embodiment, the coating may be sprayed or electroplated on the lead tip. In another non-limiting example, radiodense markers may also be applied in bands or segments along the length of the needle and/or lead to be used for identification of position and depth of lead or needle in the tissue under x-ray imaging. In another embodiment, the radiopaque markers along the length of the lead could be used to assess lead depth and track lead migration during therapy, making it easier to confirm lead placement stability for continuous therapy. As another non-limiting example, the inner and/or outer sheaths may be labeled or marked with radiopaque materials to assist with lead placement under fluoroscopy and visualization of needle depth, monitoring the respective location of needles or sheaths, and proper deployment and anchoring of the lead.

The introducing device may also enable selectively self-anchoring lead and insertion system that may place a selectively self-anchoring lead in anatomical locations that are capable of movement, including but not limited to limbs, joints, back, neck, head, abdomen, torso, face, and extremities, foster tissue ingrowth that seals the skin exit site, and prevent the lead from positioning in and out of the skin, which can further minimize infection risk.

The introducing device may also avoid interference with normal function of the body or body parts, rehabilitation, or return to normal function. As a non-limiting example, the introducing device may avoid interference with use of a joint (e.g., prior to, during, and/or following joint repair or replacement surgery) and avoid interference with use of a joint (e.g., including the original joint, repaired joint, and/or replacement joint) during post-op rehabilitation and daily activities.

Some embodiments may employ different designs to provide for different exposure of leads. In one embodiment, the opening at the distal end of the outer sheath has a beveled or slanted edge, as as seen in FIG. 9A, so that rotating the outer sheath uncovers or recovers an exposed anchor lead. This may allow a clinician to expose part or all of an anchor lead, e.g., part of a barb or tine. In an embodiment, stops could be added into predetermined locations to allow for ease in exposing a portion of a lead without deploying the entire lead. In an embodiment, a clinician could apply a rotation or a sliding type mechanism to deploy part or all of the lead. In an embodiment, the introducing device could employ a rotation technique to only partially expose the lead without fully deploying it and a sliding sheath could fully expose and deploy the lead, e.g., in a channel and/or lock design.

In one embodiment as shown in FIG. 10, the inner sheath 802 may include an inclined portion 824 that may facilitate deployment when the sheath 802 is withdrawn. This may alter (e.g., reduce) the possibility of a lead 834 being compressed or otherwise held within the sheath 802. For instance, it may reduce a possibility of the hooked, tined, barbed portion of a lead from being held or attached to the inner sheath 802. In another aspect, the inclined portion 824 may alter (e.g., improve) the ability to anchor the lead 834 at a desired location. The use of a small-diameter self-anchoring coiled or helical lead enables the duration of the lead placement and stimulation testing procedures to be minimized, limits the number of percutaneous insertions required, decreases risk to the patient, enables efficient positioning and re-positioning of the lead for stimulation testing and lead deployment, enables clinicians to position and deploy the lead correctly and optimally with minimal or no additional training, and decreases the time required to form electrical connections for testing.

Test stimulation through the introducer system requires electrical current be passed to the stimulating electrode and/or lead tip from the external stimulator. The present invention is novel and advantageous because it allows the introducer system to be coupled to the external stimulator used by the patient, ensuring the responses achieved during test stimulation (e.g., in clinic, hospital, etc) are representative of the responses to be expected and/or achieved during therapy (e.g., typical home use by the patient) and further avoids the need to reprogram the stimulator between test stimulation and home-going stimulation.

The introducing device may be removably coupled with a stimulator through the use of a lead connector. The stimulator may be powered through a battery embedded within the stimulator itself or an attached electrode.

The battery may be any appropriate size that allows for continuous delivery of therapy for consistent pain relief to the user. Further, the stimulator may be wirelessly programmable and controllable. In an embodiment, the stimulator may be wired. In an embodiment, the stimulator and introducing device may have custom wireless interfaces for the clinician and/or patient.

In an aspect shown in FIG. 11, the proximal end 512 of the introducing device 500 may include a connector plug 560 that may be coupled to a power source and/or current source (not shown). Current may be passed from the power source through the connection plug 560 and to the outer sheath 550. The current may pass through the outer sheath 550 and be applied to a tissue region at the distal end 558 of the outer sheath 550.

The present invention includes designs to facilitate the use of the lead for testing, a non-limiting example being a connector which can electrically connect the proximal end of the lead to an external stimulator via a wire quickly and effectively in a useful way (e.g., strong/stable mechanical and/or electrical connection) and which can reduce the duration of the procedure. Being able to easily remove the connector also can reduces procedure time, as upon lead deployment in the prior art, the introducer system must be withdrawn over the lead, and a connector would stop this from happening and would need to be removed as the introducer needle/sheath cannot be withdrawn over it without first disconnecting the lead. Although a simple connector (e.g., a commercial alligator clip) could be used, such a connector can be difficult to use in an operative setting with an extremely small diameter coiled lead. Clinicians or staff may have difficulty connecting the tiny end of the wire to a typical/mechanical electrical connector. A non-limiting example that addresses these issues is a custom connector consisting of a funnel which the end of the lead can easily be inserted into. The funnel guides the lead wire into the connector area, where teeth, loops, or surfaces which are spring-loaded can be manipulated by the user via levers or buttons to clamp onto and create an electrical connection with the lead. This connector could have a wire and plug attached with allows for connection with an external stimulator.

A lead connector may be designed to couple to the percutaneous lead easily. In a non-limiting example, the lead 934 may be inserted through an aperture or slot 952 in the lead connector 956, and the lead cable may go through partially or completely therethrough. The aperture may include a funnel shape where the lead 934 is inserted to enable easy insertion into the aperture, as indicated by the arrows in FIGS. 12A and 12B. In another non-limiting example, the lead connector 956 may be composed of two or more components with the lead placed between and/or within the components, and the components may be secured together (e.g., slid together, snapped in place, twisted/screwed onto one another, etc.) to couple to the lead. In some embodiments, the lead connector may enable easy one-handed insertion and coupling of the lead to the system while remaining mechanically and electrically secure and prevents the patient from decoupling the lead (or electrode) intentionally or unintentionally.

The lead may be coupled to the lead connector electrically and mechanically. The mechanism by which the lead may be coupled mechanically to the lead connector may be separate or the same as the mechanism by which the lead is coupled electrically to the lead connector. The user may couple the lead to the lead connector using a component including, but not limited to, a knob, button, switch, or dial.

The lead connector may be decoupled from the lead, and may allow the lead to be reconnected to the lead connector at a different point along the lead (e.g., closer to or farther away from the stimulating portion of the lead or electrode). In a non-limiting example, the lead connector may include a lock to prevent the patient from disconnecting the lead. The lock may be opened using, for example (but not limited to), a key, a tool (e.g., torque wrench), a code (e.g., combination) or without a tool. In another non-limiting example, the lead connector may minimize or eliminate damages or changes to the lead's structure, enabling the lead to remain sufficiently intact to generally reduce the risk of the lead fracturing or breaking and enable current flow through the entire lead. In another non-limiting example, a lead connector may be attached to the lead prior to or after insertion of an introducer system, enabling stimulation through the lead tip during the lead placement procedure. In one embodiment, the connector may be attached to the lead by dropping the lead into a slot or hole on the block and closing a flap which implements an insulation displacement connection (e.g., cutting through the insulative material aside to form a connection with the conductive lead wire). This lead connector may improve the speed and ease of lead connection because it can be attached without the use of tools (e.g., no wire cutters, scissors, and screwdrivers). For example, in this embodiment, the lead may be placed into a slot in a lead connector block and secured using a lockable, reversible one-handed mechanism to displace the insulation on the lead body. The insulation displacement mechanism inside the lead connector may also cut the lead distal to the electrical connection. Once the connection has been made and the excess lead is trimmed, a lock (e.g., sliding, twisting, button press) may ensure that the flap on the block cannot be reopened accidentally. This feature prevents loss of connection between the lead connector and lead, which would result in loss of therapeutic benefit. The lead connector may mate with another lead connector (e.g., lead or plug to the stimulator) to complete the circuit from the stimulator to the lead tip electrode.

In one embodiment, the connection between the two lead connectors may be magnetic. In this case, the shape of the lead connectors will prevent improper alignment of the lead connector (e.g., lead connectors that only fit together in one orientation). The magnetic connection may be used for both temporary and permanent stimulation delivery (e.g., during lead placement procedure or during patient's home use of the therapy). After obtaining proper lead placement location, the lead connector block may be removed and replaced following removal of the introducer system needle(s) and sheath(s). In one embodiment, the connection may be deactivated by pressing or sliding open the slot that contains the lead. In this example, the lead connector block may be removed or cut off prior to removal of the introducer and then quickly re-attached to a more proximal location on the lead. Following removal of the introducer, the lead may be placed in the slot and connected with a one-touch mechanism (e.g., pressing, sliding) and then the lead connector may be attached to the stimulator cable.

The magnetic connection may act as a quick-release connection that will prevent accidental lead (or electrode) dislodgement due to a pulled lead and/or lead. Instead of transferring force to the lead exit site and lead, any forces on the lead will be discharged due to the breaking of the magnetic connection between the lead and lead connector block. If desired by the clinician, a permanent connection may be made by locking the two-connector pieces together using a press button lock (or any other suitable lock). In addition to mating with the lead connector block, in another embodiment, the magnetic cable connector for the stimulator may also mate with an identical version of the lead connector block, which is connected to the test stimulator via a cable. In another embodiment, the magnetic cable connector originating from the stimulator may be bifurcated to connect with multiple lead connector blocks (e.g., to enable stimulation of two leads with one stimulator).

The present invention may reduce lead placement procedure discomfort by limiting the diameter of the percutaneous system. Resistance to insertion through skin or tissue skin may cause additional pressure to be placed on a patient's skin and/or the device, leading to potential discomfort (e.g., pain or bruising from the pressure of insertion or from multiple failed attempts to insert needles) and/or damage or strain on the device (e.g., damage to lead or introducer, lead deployment mechanism failure). Reducing the resistance to insertion may be accomplished by limiting the diameter of the introducer system, designing or manufacturing the needle to be sharper (e.g., sharper edges of heel and/or additional bevels), or coating the surface (e.g., exterior shaft) of the needle(s). Modifying the bevel shape or sharpness of the needle(s) in the introducer system (e.g. by the addition of multiple bevels during needle manufacture or grinding or shaping the needles) may make insertion easier (e.g., requiring less force) and ensure that the lead placement procedure is more comfortable for the patient. Multiple bevels and increased needle sharpness are advantageous because these minimize risk to patient, enable reliable insertion, and enable insertion that avoids unnecessary pressure on the lead or device. In another embodiment, a coating may be partially or completely applied along surfaces of the introducer needle(s) to reduce resistance to insertion through tissue (e.g., polymeric coating that glides through tissue easier). In one embodiment, the coating may be hydrophobic (e.g., polytetrafluoroethylene, silicon rubber), hydrophilic (e.g, polyvinylpyrolidone, polyurethanes, polyacrylic acid, polyethylene oxide), or liquid-impregnated to improve ease of insertion and maneuverability within tissue by reducing friction between skin or tissue and the needle. Modifications of the exterior of the needles that minimize insertion force required by clinicians (e.g., enabling lead placement by clinicians) and that do not produce a substantial increase in outer diameter will ensure that selective lead deployment may be performed through minimally invasive approach, using a minimal number of insertions and further minimizing risk and discomfort for the patient.

One way to limit and/or minimize the diameter of the system is through the use of a needle/sheath with a portion along the inner wall of said needle/sheath removed such that space for the lead anchor is allowed. Examples of such configurations are illustrated in FIG. 9B. The portion of the wall N of the needle/sheath 150 is removed/made thin advantageously such that the lead anchor 134 can be contained (e.g., 1-10 mm of the wall along the length of the needle starting from the proximal end of the bevel, preferentially 5 mm, with a width sufficient to allow the anchor to be contained (e.g., 0.1-0.5 mm, preferentially 0.2 mm), but the mechanical strength of the needle is minimally impacted. In a system consisting of two needles/sheaths, this could also be realized by removing some of the inner needle's outer wall (not shown in FIG. 9B) in a similar fashion, or by doing both such that some of the outer needle and some of the inner needle walls are removed to form a complete slot for the lead anchor to be contained within.

Another example illustrated in FIG. 9B is to use a plastic inner tube P that is stiff enough to allow for deployment, but flexible enough that the outer anchor hook (not shown in the perspective views) can press in the plastic sheath's end, allowing the outer needle to be just larger than the inner tube and to completely contain the un-deployed lead. The flexible plastic sheath would also have to be flexible enough that it could be withdrawn over the lead without catching. Avoiding having the lead catch within an inner tube would be an important issue in these diameter limiting solutions where the inner needle may lead little space around the lead, which could lead to an excess of friction. A non-limiting example of a solution for this would be the use of a biocompatible lubricant applied between the parts that must move relative to each other, such as a silicon based (or other appropriate) lubricant With reference to FIGS. 9C and 9D, embodiments of this invention have a slot or window S ground, cut, or otherwise produced in the sheath/needle 102 such that the end of the anchor of the self-anchoring lead 134 can re-enter the lumen of the needle/sheath, allowing a second sheath/needle or containment mechanism to be positioned over the portion of the anchor which re-enters the lumen of the needle, thereby securing the lead to the testing/introducing system until such a time as it is desired that the lead be deployed. Desirably, this embodiment of the invention can be combined with one or more of the other examples described, including but not limited to delivering stimulation through the distal anchor of the self-anchoring lead and/or the use of one or more contact electrodes in the outer sheath used for delivery of test stimulation. Note that in FIG. 9C, the system 100 is shown in various stages of its assembly, with inset (a) showing only the inner sheath, inset (b) showing the sheath 150 and lead/anchor 134, and inset (c) showing the inner sheath 102, lead anchor 134, and outer sheath 150.

Reducing the outer diameter of the system is desirable as this limits the discomfort experienced by the patient during the procedure. In the example in which a sheath over a needle is used to secure the lead anchor of the self-anchoring coiled lead in place during placement/testing/repositioning, a tight fit of the outer sheath over the inner needle, which would both limit the outer diameter and better secure the lead anchor, could be accomplished by using a sheath material that could be shrunk, for example by application of heat or other means of causing the sheath tubing diameter to contract. This can also ease the manufacturing and assembly burden of this system, as a tightly fitting sheath would not have to be threaded over the inner needle and the lead anchor. The larger diameter outer sheath could easily be slid into position and then shrunk to provide a tight fit.

Desirably limiting the outer diameter of the system which is inserted percutaneously or through the skin may be embodied such that pain and/or discomfort during insertion, stimulation testing, and/or deployment of a self-anchoring migration-resistant lead is minimized may be preferentially embodied by utilizing thin-walled needle(s) or sheath(s) to contain the lead during placement/testing/deployment. The use of one or more needles or sheaths of an appropriate material (e.g., metal, plastic) with a wall thickness that provides adequate lumen space for containment of the lead, minimizes the outer diameter of the system, and provides sufficient resistance to bending and/or other forces to which such a system is subjected during lead placement and testing procedures is desirable and advantageous. The preferred embodiment of the described invention utilizes one or more thin-walled needles/sheaths as described in combination with one or more of the examples and embodiments discussed which also enable the invention to minimize the duration of the lead placement and stimulation testing procedures, limit the number of percutaneous insertions required, decrease risk to the patient, enable efficient positioning and re-positioning of the lead for stimulation testing and lead deployment, enable clinicians to position and deploy the lead correctly and optimally with minimal or no additional training, and decrease the time required to form electrical connections for testing.

A close fitting sheath over a needle may pose potential problems for lead deployment, for example the sheath may adhere to the surface of the needle more strongly than anticipated such that movement of the sheath over the needle is prevented or requires such force that the device is either unsafe or not user friendly and can additionally cause a delay or extension of the procedure. A non-limiting example of overcoming this problem is to apply a lubricant between the sheath and the needle such that sliding of the sheath over the needle is enhanced or requires less or minimal force. This lubricant could be based on a silicon jelly, but also could be realized of other appropriate materials. Another non-limiting example of a way to overcome this problem is to have a mechanism by which the sheath can be split open. This can be accomplished by having a thin wire embedded in the sheath which can be pulled upon during lead deployment and which causes the sheath to split open allowing the lead anchor to release. These aspects of the invention can beneficially be combined with other embodiments of the invention described.

Another embodiment of an aspect of the present invention to overcome the potential problem of inappropriate adhesion of components to one another is described in a non-limiting example as the use of a manufacturing method wherein a placeholder(s) is used during manufacture of various of the close-fitting components (e.g., a placeholder such as a solid metal wire preferentially the slightly larger than the diameter of the lead used during the manufacture/fitting of various components designed to secure the anchor of the lead (e.g., an outer sheath with or without a slot or section removed or ground out specifically to contain the lead anchor)). This is advantageous as it allows the final components to fit together tightly/securely, but prevents overly tight fitting such that deployment and/or positioning and/or testing is impeded or hindered.

The present invention may prevent/reduce user mistakes and mishaps during lead placement and stimulation testing by allowing for one-handed lead placement and deployment. For example, the lead deployment mechanism(s) can be manipulated with one hand such that the other hand is not required to cause the lead to deploy. Such an embodiment is advantageous as it both reduces the difficulty for the clinician to utilize the system and allows the clinician to use the other (non-deploying) hand for another purpose, for example to manipulate an ultrasound probe during lead deployment such that the position of the lead can be observed. This can be advantageous as it can be used to reassure the clinician in real time that the distal anchor of the self-anchoring lead maintains the desired location during lead deployment and/or withdrawal of the testing/introducing system. As non-limiting examples, the preferred embodiment of a lead deployment mechanism can consist of a lever(s), button(s), gear(s), slider(s), push button(s), twisting knob(s), handle(s) with gripping surfaces for pulling or pressing on, handles/levers which squeeze together and/or other means of mechanically and/or electrically actuating the deploying component(s). Examples of embodiments of the deploying component(s) (e.g., an outer sheath and/or an inner stylet or core) are described in other sections, and one or more of these may be beneficially combined with one or more of the lead deployment mechanisms such that the clinician can easily and effectively control the deployment of the self-anchoring lead.

In one embodiment of the invention, the placement and repositioning of the lead is aided by design elements which enhance the controllability or the ease with which the clinician can handle the system during percutaneous placement, withdrawal, and/or repositioning of the system before, during, and/or after stimulation testing and lead deployment. Such an embodiment may limit the procedure time, thereby providing significant benefit to both the patient and the clinician. A non-limiting example of such an embodiment is the application of ergonomic, gripping, textured, and/or other tactile features which can be located on the proximal end of the needle/system and/or on the deployment mechanism(s) to ease the placement of the lead through the skin and tissue of the patient, as seen in FIG. 13. Such an embodiment can provide significant benefit to patients with tough or thick skin, as the clinician may otherwise have difficult applying the necessary pressure to quickly insert the system through the skin at the desired location.

Figure 14A:
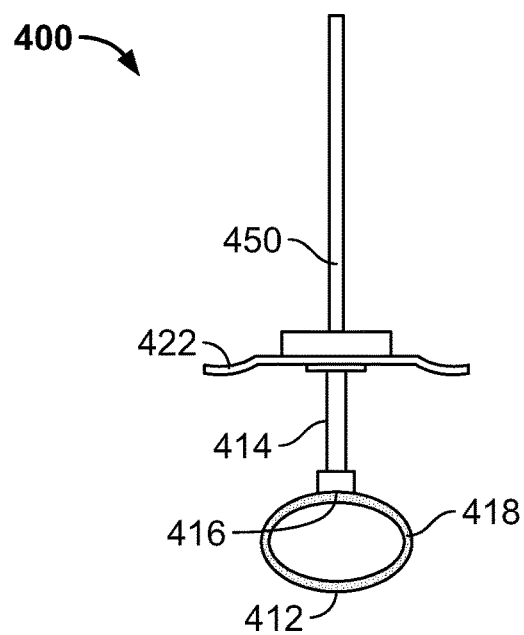
Figure 14B:
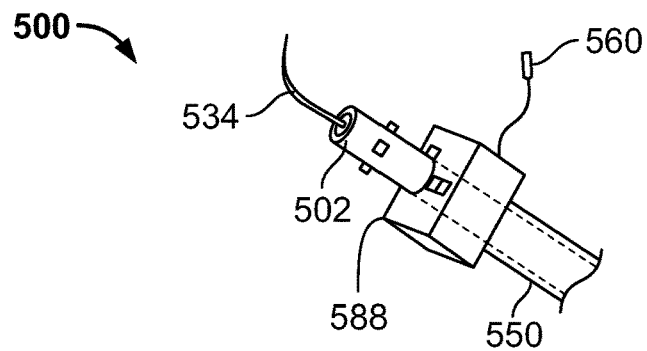

FIGS. 14A and 14B show embodiments of the introducing devices 400, 500. In an aspect as shown in FIG. 14A, the introducing device 400 includes a proximal end 412 having a body 414 with a lock 416. The body 414 may be comprised of any appropriate material, including polymers, metals, stainless steel, or a combination of two or more thereof. The lock 416 may be any appropriate type of lock or stepper, including, but not limited to, a lever, trigger, plunger, button, wheel, switch, threaded member, or the like. When engaged, the lock 416 may prevent the inner sheath from advancing or moving at all. This may occur through the use of a threaded system, locks, steppers, etc. By releasing the lock 416 through pushing, pulling, twisting, or any other appropriate mechanism, the inner sheath may disengage from the lock system and can advance forward, e.g., out of the outer sheath 450. As the inner sheath advances, a lead may be deployed. The lock 416 may be comprised of any appropriate material, including polymers, metals, stainless steel, or a combination of two or more thereof. The lock 416 may be comprised of the same material as the body 414 or they may be comprised of different materials. The body 414 include a loop 418 and a grip 422 configured to engage with a clinician's finger(s) during use. The loop 418 may be engaged with the lock 416, and when engaged, may allow for the movement of the inner sheath out of the outer sheath 450.

The grip 422 may be comprised of any appropriate material, including polymers, metals, stainless steel, or a combination of two or more thereof. The grip 422 may be designed to support the clinician's fingers, and therefore may be etched or have a rubberized or comfort service for improved traction and comfort of the user.

In an embodiment, the body 414 may include several loops configured to engage with a clinician's fingers during use, e.g., the thumb, and the pointer and ring fingers, or for a different user, the thumb, the pointer and the middle fingers. In an aspect, the body 414 may not include any loops.

Figure 14C:
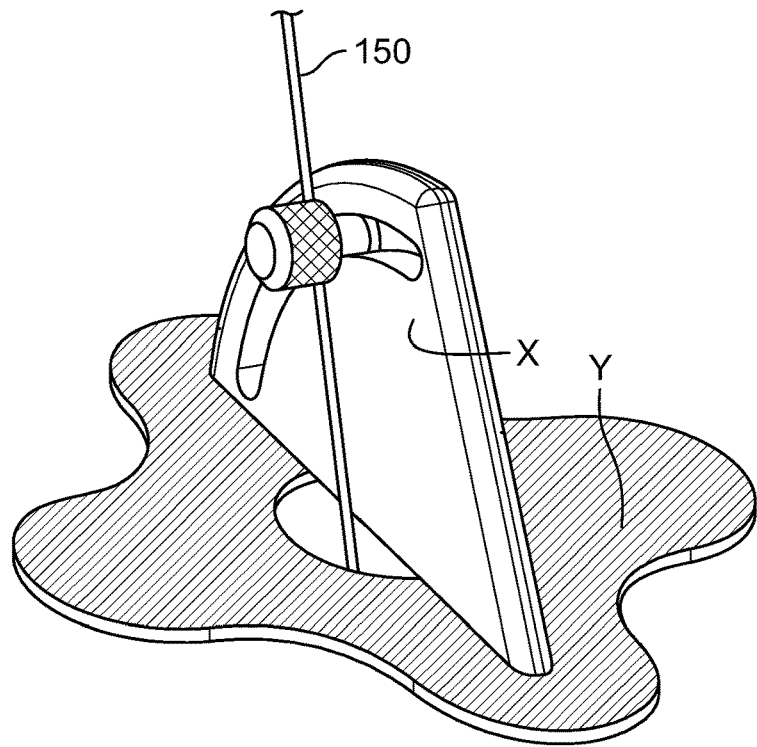
Figure 14D:
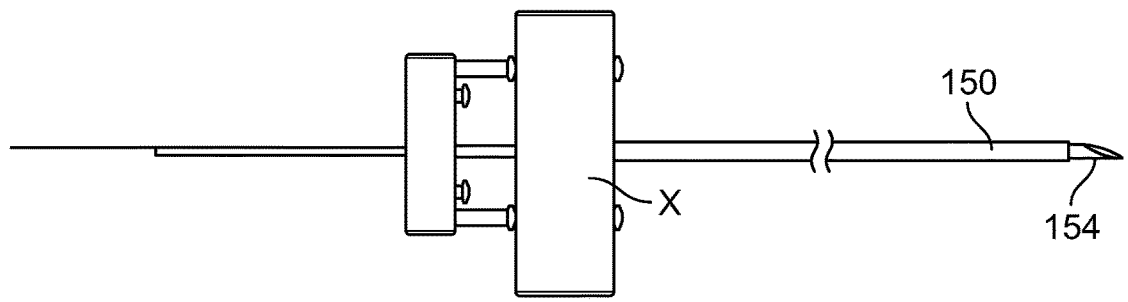
Figure 14E:
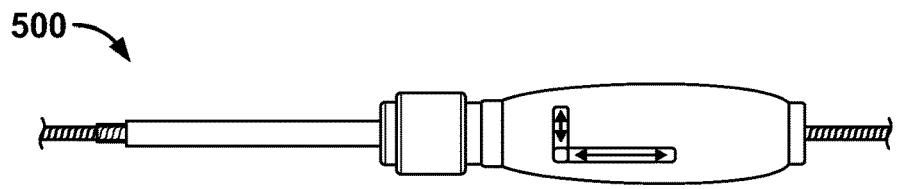

Lead deployment may also be initiated through a lock or stepper on the proximal end 512 of the introducing device 500, as seen in FIGS. 14B and 14E (with the latter generally showing device 500 along with arrows indicating the anticipated range of motion). By releasing the lock or stepper, the inner sheath 502 could be advanced by pushing or by use of a lever, button, wheel, switch, threaded members, or the like. The inner sheath 502 may have locks or steppers to prevent the inner sheath 502 from deploying too far. The end of the inner sheath 502 may be open so it can be withdrawn over the deployed lead anchor 534 and potentially a microlead. The system helps to prevent user mistakes and/or mishaps during lead placement and stimulation testing of a self-anchoring lead, while reducing or limiting procedure duration is one in which the positioning of the system can be maintained securely throughout the procedure regardless of the depth and which the lead and introducing/insertion/testing system has been inserted. Prior art relies on the resistance of the tissue to maintain the position of the insertion system and self-anchoring lead during testing procedures, raising concerns when the system is placed insufficiently deep in the tissue to allow for the tissue to prevent movement of the system. Non-limiting examples of embodiments which maintain the introducing system position throughout testing and/or lead deployment are described in the following sections such that the various embodiments can provide additional significant benefit with combined with one or more of the other embodiments/examples described throughout the invention description As seen in FIGS. 14C and 14D, the system, and more specifically the needle 150, is inserted into the target tissue/through the skin. The needle is mechanically secured to a component X which is, in turn, able to be secured/fastened to the body/skin of the patient, by way of an adhesive Y as one example. The component is secured to both the system and the patient's body such that the system is securely held in place relative to the patient until such a time that the clinician determines the system is to be repositioned and/or removed. The component may connect to the system via any appropriate mechanical connection which can be secured and/or removed with minimal expenditure of time and effort (e.g., a clamp, lock, twisting, or other securing mechanism). Additionally, the component may connect to the patient's body via any appropriate mechanical connection which limits discomfort to the patient and can be secured and/or removed with minimal expenditure of time and effort (e.g., tape, bandage, gel, hydrogel, or other securing mechanism compatible with temporary use on skin). The component can be secured to both the patient and the system such that movement of the system relative to the patient's body is minimized during test stimulation procedures and/or lead deployment.

In this non-limiting example, a component such as the one described above which mechanically mates the system for the introduction/insertion of the self-anchoring lead and the delivery of test stimulation with the patient's body is implemented such that the component can be freely rotated relative to the patient's body while locked in position relative to the system until the desired locking position is determined. Alternatively, the component may be locked relative to the patient's body while allowing free rotation/positioning of the system prior to locking in the final positioning. Such a component can also allow the positional locking/securement to be released as necessary for system repositioning or removal.

The component X described above mechanically mates the system for the introduction/insertion of the self-anchoring lead and the delivery of test stimulation with the patient's body is implemented such that the component is secured in place to the patient's body, and the component incorporates a mechanism which allows the angle of the lead insertion/stimulation testing/lead deployment system to be adjusted and locked into position as desired. Such a component can also allow the positional locking/securement to be released as necessary for system repositioning or removal.

The present system includes designs to objectively reposition the percutaneous system. A potential problem with delivering test stimulation via a system wherein the anchor of the lead is partially or fully contained is that the lead may inadvertently become deployed by moving the inner and/or outer needle and/or other method of deploying the lead in an unintended fashion or relative distance (e.g., the lead is advanced further than intended or at an unintended time). A system by which the inner and outer needle (or other deployment mechanisms such as a stylet) relative positions can be locked, stopped, or visualized during insertion, testing, and/or deployment is one example of a way to reduce this risk. One embodiment of this solution is to have a series of stops in the proximal portion of the deployment system which allow the needles to be positioned relative to each other by twisting, pushing, clicking, rolling, sliding, or other means of control with a lever, locking mechanism, or other means.

This non-limiting example of an embodiment of the invention which allows for objective repositioning of the percutaneous system consists of mechanical and/or visual markings which display the relative positions of the percutaneous introducing system and the lead and/or a stylet and/or an inner sheath/positioning mechanism. Such markings may make known the position of the lead relative to the a position in the introducer (e.g., distance of the distal end of the lead from the distal end of the introducing sheath) and/or the position of the end of the introducing system in the tissue/body (e.g., the depth distal end of the introducer system and/or the angle relative to the skin at the insertion/entry site). An alternative or complementary marking embodiment may include clearly marked positions (e.g., markings for deployed, locked, and/or other desirable system and/or lead positions). Such an invention may preferably combine these aspects of the embodiment, allowing the depth and angle of the introducer system and the lead relative to each other and/or the skin/insertion site to be readily discernible. Such an embodiment allows for objective repositioning of the percutaneous system, and may be incorporated with one or more other examples discussed in this disclosure such that the duration and the difficulty of placing a helical, migration and infection resistant lead in an optimal location is reduced or limited. It may comprise a plurality of arc-shaped channels positioned orthogonal to one another. One or more screw, clip, or spring-loaded pins cooperate within the channels (possibly including slots or other predetermined points along the arc or arcs) to fix the position of the angle and rotation of the introducer needle relative to the surface of the patient's skin (i.e., the site of injection for the needle).

The present invention includes designs to objectively reposition the percutaneous system. A potential problem with delivering test stimulation via a system wherein the anchor of the lead is partially or fully contained is that the lead may inadvertently become deployed by moving the inner and/or outer needle and/or other method of deploying the lead in an unintended fashion or relative distance (e.g., the lead is advanced further than intended or at an unintended time). One embodiment of this solution is to have a series of stops in the proximal portion of the deployment system which allow the needles to be positioned relative to each other by twisting, pushing, clicking, rolling, sliding, or other means of control with a lever, locking mechanism, or other means. Such an embodiment may allow for the lead to be moved into several different positions such as, but not limited to, a locked/secure position for insertion, a partially deployed position for testing, a withdrawn position for re-positioning, and a deployed position. Such an embodiment allows for objective repositioning of the percutaneous system, and may be incorporated with one or more other examples discussed in this disclosure such that the duration and the difficulty of placing a helical, migration and infection resistant lead in an optimal location is reduced or limited.

In the non-limiting example of concentric needles or sheaths, a mechanism is needed to control the movement of the needles and sheaths with respect to each other and the surrounding tissue, ensuring proper location of lead deployment and avoiding damage to the lead. Selective lead deployment may be accomplished by sliding the outer needle to expose the bevel of the inner needle and the tip of the lead and a retraction of the needles to position the lead tip or anchor into the nearby tissue. However, in this non-limiting example, an apparatus to control distance of needle movement is critical for precise lead placement and to ensure that the needles do not move or slide in relation to each other prior to or after the deployment of the lead to prevent shearing, fracturing or bending the lead or lead tip.

In order to achieve this level of control, a spacer or place-holding mechanism S as shown in FIGS. 15A and 15B may be used. These spacers lock the two needles together during insertion through the skin by the clinician and then enable deployment of the lead at a desired location. In one embodiment, the spacer may be composed of a partial or complete cylinder and located between the hubs of the inner and outer needles. In such an embodiment the spacer may be removable, with threads on the ends that enable the spacer to lock onto the hubs of each needle (for example, the spacer may be removed by twisting the spacer past the threads on the needle hubs and sliding the spacer off). In another embodiment, the spacer may remain in place and collapse in order to permit retraction of the external needle. For example, in this embodiment, twisting or pressing a button on the spacer (as indicated by the arrows) would enable the spacer to be condensed, allowing for directed retraction of the external needle.

In another non-limiting example, the needle hub of the external needle or internal needle may be retracted a specified distance into the handle of the introducer. In another non-limiting example, a component of the introducer handle may be twisted to retract any of the needles, sheaths or leads a specified distance. This would permit controlled retraction of the needle and enable correct placement of leads. In one embodiment, the handle to control the retraction and movement of needles may be ergonomically designed with smooth contours to fit in the hand of the clinician and buttons or sliders to enable single hand operation of the introducer system. Single handed operation further will enable proper lead placement, for example, allowing the clinician to visualize the target with ultrasound with one hand while advancing, retracting or repositioning the introducer system and then deploying the lead with one hand. Additionally, the handle of the introducer could be marked to illustrate the direction or side of the needle where the lead will be deployed to further assist the clinician with proper placement of lead.

In a non-limiting example of an introducer with multiple stimulation electrodes, the components of or the entire system could be retracted to the desired location of effective test stimulation, the external needle retracted and the lead tip deployed. Here, the lead may be deployed at any location along the length of the external test needle without having to redirect the needle. A slit or opening along the length of the external needle (also as described above) would permit the lead to be repositioned without having to move the exterior needle. In this embodiment, the lead may be repositioned with an inner sheath or needle that enables the lead to be repositioned inside the needle and then deployed at any depth along the needle.

A non-limiting example is an embodiment in which multiple contacts could be positioned on the introducer at specific intervals so that there may only need to be one needle insertion and one repositioning of the insertion/testing system prior to lead deployment. In a non-limiting example, contacts are spaced (e.g. 1 mm) (+/−) on the outer needle. The needle may be inserted to Y mm (e.g. 5 mm) from the nerve. Test stimulation can be delivered from each contact individually or in combination as desired or needed, for example starting with the most distal contact. If stimulation at the $Z^{th}$ (e.g. $4^{th}$) contact provides the optimal response, the clinician can then withdraw the introducer system Z mm (e.g. 4 mm) and deploy the lead (with or without testing again—both or either of which could be desirable in various scenarios, making it potentially advantageous to provide the option to the clinician).

In another non-limiting example, there could also be software to accelerate, expedite, or automate this process, including the process of delivering test stimulation at multiple contacts sequentially. In a non-limiting example, once information such as calibration point(s) or a range(s) (e.g., a range of physiologic responses to a range of stimulation intensities, a range of distances from the target or non-target tissue(s), etc.) is known from testing the first (or other) contact(s), the software could enable testing to be progressively faster or more expeditious for subsequent contacts. There could be advantages to not having it completely automated (e.g., ensuring stimulation does not produce unwanted responses such as pain, discomfort, or unwanted muscle contractions).

The present invention may prevent/reduce user mistakes and mishaps during lead placement and stimulation testing by incorporating patient feedback automatically during stimulation testing via a patient controlled testing system, simplified parameter testing procedures, and/or a system which requires only patient feedback to operate. This can advantageously reduce both the time of the testing procedures and/or can limit the number of position changes the system may require before locating the optimal or desired lead deployment position.

A non-limiting example which incorporates patient feedback into stimulation testing is one in which test stimulation is controlled by the patient. A controller (e.g., hand-held remote, tablet, smartphone, or other appropriate interface) is handled by the patient which may be capable of delivering stimulation currents directly to the test stimulation system via a cable or may control a stimulus generator via wired and/or wireless technology (e.g., Bluetooth, RadioFrequency). In turn the generator is mechanically and/or electrically connected to the test stimulation system such that electrical stimulation currents can be delivered through the system to the target tissue. The patient controller may allow the patient to adjust one or more parameters (e.g., pulsewidth, amplitude, frequency, and/or waveform of the electrical current/signal/test stimulation) such that the patient is able to obtain the desired physiological response (e.g., paresthesias, muscle contractions, and/or pain relief). Alternatively, such a controller may be handled by a clinician with adjustments being made based on the results of the test stimulation (e.g., based on verbal feedback from the patient, visualization of contraction directly and/or via ultrasound, and/or clinical experience). The non-limiting examples described here may advantageously be combined with one or more of the examples/embodiments of the described invention.

Where stimulation testing is controlled by the patient, one aspect of the invention (reducing overall procedure duration) may be hindered by stimulation testing controls and/or parameters which are complicated and/or provide patients (or clinicians) with more options than necessary to test and identify the optimal or desired lead deployment location. These risks may be minimized by simplifying the methods and/or the controls for adjusting parameters during stimulation testing. FIG. 16 indicates a number of parameters (i.e., pulsewidth and amplitude of the stimulation) and how these parameters might be adjusted by the patient controller. As represented by the linear arrows in each of the insets (a) through (c) of FIG. 16, only a limited number of inputs/buttons/knobs/controls (e.g., 1 to 5 function features, and more preferably 3). These inputs correspond to the ability to increase and/or decrease the parameters as shown in FIG. 16. In one embodiment, a single button increases one or more parameters (e.g., pulse duration, amplitude, frequency, and/or a combination of parameters), another button decreases one or more parameters, and a third button enables test stimulation to be turned on and off. The control can be advantageously calibrated or designed specifically for a given type or style of stimulation (e.g., high or low frequency, causing or avoiding muscle contraction vs. sensory nerve fiber activation, etc.) prior to use during the placement and testing procedures.

Additionally or alternatively, patient feedback may be incorporated into the testing procedures through the use of software/programming that adjusts test stimulation parameters based on input/feedback from the patient and/or the clinician. Such adjustments enable the testing procedure duration to be minimized, while simultaneously avoiding any potential uncertainty regarding stimulation parameter adjustments. In this non-limiting embodiment, the patient and/or clinician obtains feedback using a graphical interface mechanism, such as a controller or tablet GUI as shown in FIG. 17, that allows information regarding the results of test stimulation to be relayed to or communicated with the stimulus generator. Such a controller could include, for example, a inputs by which sensations (e.g., paresthesias), pains, and/or contraction intensity may be communicated by the patient to the clinician, as well as the location of such sensations, pain, or contractions on the patient's body. For example, tablet GUI display an image representative of a portion or all of the patient's body and which allows the patient to select/highlight/draw or other means of making known the areas which in which stimulation is felt/seen/results in some outcome. Software determines appropriate adjustments to the test stimulus parameters and/or recommends to the clinician how to re-direct or reposition the system to a new test location and/or where to deploy the lead (e.g., in the current location, in the new test location, etc.). Such a program, system, and/or method may be combined with one or more of the other embodiments of this invention such that the combination is advantageous for the purposes of the invention.

An exemplary stimulator may be able to provide at least the following parameters: amplitude of 0.2-20 mA; pulse duration of 10-200 μs; and frequency of 5-100 Hz. The stimulator may be connected to software for wireless clinician programming of the therapy, software and hardware for a wireless patient controller, and firmware and hardware for a miniature body-mounted stimulator. This arrangement allows for the clinician and patient to view and adjust treatment parameters without having to interface with the stimulator directly. This can prevent a patient from having to remove clothing, etc., to reach the stimulator during use. In an embodiment, the stimulator may communicate via physical cables, wires, Bluetooth, or other wireless technologies. The present teachings are not limited to any particular configuration.

The patient controller may also provide a more extensive graphical user interface including a variety of other options (e.g., profiles specific to a time of day/type of pain/type of anticipated patient activity, access to information on pain management, means for communicating with a medical professional, etc.), thereby making it the primary means of initiating and altering the therapy. As with the stimulator, the controller communicates via physical wires/cables or wirelessly with the stimulator (or stimulators, if multiple stimulators are included in the system) and the optional programmer unit, described below. The controller may be relatively larger than the stimulator, although wireless connectivity would allow the user to carry the controller in clothing and/or generally at a convenient distance and location in comparison to the electrode 934 and stimulator. The connections between the controller, stimulator, and introducer system may include any of those described herein (e.g., standard wired connections, wireless connections—particularly between the controller and the stimulator, wired connections relying on quick release mechanisms, etc.)

The stimulator allows for adjustment of stimulation intensity by controlling stimulation amplitude and pulse duration, preferably with a single programmable parameter for intensity. Stimulation intensity itself may be determined by multiple parameters, including (but not limited to) stimulation amplitude and pulse duration. For example, stimulation intensity may be increased by increasing stimulation amplitude, pulse duration, or a combination of the two. Controlling multiple parameters such as stimulation amplitude and pulse duration using a single parameter may reduce the complexity of the procedure to program stimulation parameters by reducing the number of parameters that can be changed from 2 or more to 1. As a non-limiting example, the minimum of the stimulation intensity parameter (e.g., 0) may set the stimulation amplitude and pulse duration to their lowest values (e.g., 0.2 mA and 10 microseconds). As another non-limiting example, increasing the stimulation intensity parameter may change the stimulation amplitude, the pulse duration, or both.

In yet another embodiment, increasing the stimulation intensity parameter from the minimum value may first increase the stimulation amplitude while keeping the pulse duration at a minimum until the maximum value of the stimulation amplitude (e.g., 20-30 mA) is reached. Then, continuing to increase the stimulation intensity parameter may keep the stimulation amplitude fixed at the maximum value while increasing the pulse duration until the maximum value of the pulse duration is reached. In these embodiments, stimulation intensity is simple to program and may be increased while keeping pulse duration as low as possible, so as to keep the stimulation charge required to activate nerve fibers as low as possible and to increase the patient/clinician's ability to selectively stimulate large diameter fibers over small diameter fibers. In another non-limiting example, increasing the stimulation intensity parameter from the minimum value may first increase the stimulation amplitude while keeping stimulation amplitude at a minimum. Then, continuing to increase the stimulation intensity parameter beyond the maximum value of pulse duration (e.g., 200 microseconds) may keep the pulse duration fixed at the maximum value while increasing the amplitude until the maximum value of the stimulation amplitude is reached. In this example, stimulation intensity increases while keeping stimulation amplitude as low as possible, which keeps the power consumption of the pulse as low as possible for a given charge per pulse.

FIG. 18A is the first example given, keeping pulse duration low. FIG. 18B is the second example, keeping stimulation amplitude low.

The introducer system described herein may also reduce the risk of problems following lead placement by reducing the risk of lead fracture. This risk reduction results from the shape of the electrode itself, both in terms of its self-anchoring, migration-and-infection-resistant small diameter helix/coils and its distal anchoring system, and from the reduced levels of stress imposed upon the lead during the insertion and test stimulation process by way of being able to retract and protect the electrode during insertion and repositioning.

Other advantages include the ability to enable the duration of the lead placement and stimulation testing procedures to be minimized. The system also limits the number of percutaneous insertions required, decreases risk to the patient, enables efficient positioning and re-positioning of the lead for stimulation testing and lead deployment, enables clinicians to position and deploy the lead correctly and optimally with minimal or no additional training, and decreases the time required to form electrical connections for testing. As a result, the therapy can be delivered to patients by clinicians in settings/scenarios that were previously burdensome, not practical and/or not possible (e.g., to treat pre-operative, pen-operative, and/or post-operative pain). This introducer also overcomes limitations of previous systems by minimizing or eliminating the need for: a) the insertion via multiple percutaneous devices; b) re-positioning of the lead; and/or c) extended periods of time required for test stimulation and/or lead placement procedures.

One embodiment consists of increasing the strength of the coiled/helical lead, for example by incorporating one or more strands of high tensile strength materials (such as but not limited to MP35N, nickel-chromium-molybdenum super alloy) into the lead. Adding such strand(s) and/or replacing current lead wire strand(s) with such strand(s) or wire(s) increases the fracture-resistant capabilities of the lead, increasing the utility of self-anchoring, migration and infection resistant small-diameter coil/helix leads for use in electrical stimulation systems.

Another non-limiting embodiment consists of improving the strength of the lead by adding a new strand/filament within the open core/center of the helically coiled lead. In this non-limiting example, the new strand/filament would not completely fill the opening. There would remain a gap between the outside of the new strand/filament and the inside of the coiled wire. Moreover, this new strand/filament would not extend the entire length of the coiled lead. In this non-limiting example, these two provisions help the lead remain flexible with both axial and radial forces during normal use. When the lead is withdrawn, as the coiled wire straightens out, the inner diameter of the coils of the lead will reduce and the coiled wire becomes bound to the central strand/filament. Thus the lead has a higher tensile strength and reduced flexibility during the removal process compared to the normal use configuration. The new strand/filament in the core could be a metal (e.g., 316L or MP35N) or it might be a polymer (e.g., Aramid). Such an embodiment could advantageously combined with other aspects of the disclosed herein (e.g., the use of stylet proximate to—or even as part of—the strand/filament).

As noted above, the risk of lead fracture before, during and/or after peripheral nerve stimulation therapy with self-anchoring, migration and infection resistant small-diameter coiled/helical leads is minimized because the stresses placed upon the lead during the lead placement, testing, and/or repositioning and deployment procedure are limited. A non-limiting example of an embodiment which leads to such a reduction in mechanical stress is a design which incorporates contouring (e.g., rounding or smoothing) of the inside edge of the needle/sheath which may contact the lead where it exits the bore/lumen of the needle/sheath.

Prevention of fracture and/or damage to any portion of the lead and/or self-anchoring electrode tip is critical to ensure maximal therapeutic benefit and reduce risk of adverse events for patients. The innovative, coiled lead was designed to move with tissue and skin and protects against fracture while in tissue during therapy. However, methods to eliminate other detrimental forces encountered by the lead during lead placement may further reduce the risk of lead fracture, improving safety of the system and avoiding need for lead replacement. This may be accomplished through approaches designed to reduce the force applied and/or transferred from the needle to the lead and/or anchor tip during insertion of the lead and changes to methods for manufacturing of the anchor shape to reduce strain on wires in the lead.

For example, the boundaries of the needles and/or sheaths (e.g., heel, rim, edge, bevel) may be smoothed or rounded off to prevent sharp contact with a portion of the lead and/or other component of the introducer (e.g., sheath, balloon, which may be negatively impacted by sharp edges of the needle or sheath). In one non-limiting example, manufacturing and/or fabricating the introducer needle heel with rounded the edges (e.g., by grinding, sanding or smoothing the surface) would eliminate sharp edges that may be pressed against or come into contact with the lead, which weakens the mechanical or electrical connections in the lead, thereby reducing the risk of lead fractures. The design and use of rounded edges in the introducer prevents the occurrence of fractures or strains resulting from a lead constrained against a sharp edge (e.g., heel of the needle) during insertion, which may weaken the tensile strength of the lead and result in lead fractures. The lead may alternatively be manufactured to reduce the likelihood of lead fractures by reducing the strain placed upon the lead tip during the creation of the lead anchor. In the prior art, the anchor was fabricated using uninsulated lead anchor (e.g., by folding it to produce a sharp bend), creating a point of high strain at the bend (e.g., anchor, hook) in the lead. To prevent this point of greatest strain, the lead anchor may be manufactured by gradually rolling the lead around a ball or pulley-type system to generate a curve-shaped (e.g., rounded) anchor in the lead that is free of a sharp bend. In another embodiment, the curved self-anchoring lead tip may be used to secure the lead into tissue following deployment during lead placement. Alternatively, the lead anchor tip may be manufactured in other shapes (e.g., straight, rounded, coil, serpentine), which enable the lead to be deployed and anchored in tissue, improving the strength and performance of the wires due to manufacturing that avoids sharp bends in the lead tip.

The inner and/or outer needles of the present introducer system use fully rounded edge surfaces that may come into contact with the lead. The fully rounded shape is carried through the entire cross sectional shape (e.g., by maintaining a substantially constant radius) in order to eliminate or reduce risk of lead impingement, which could subsequently increase risk of lead fracture. The use of rounded or approximately rounded edges, optionally coupled with elimination of edges or sharp pinch points on the lead in the introducer and throughout the insertion process, increases the reliability and performance of the lead and improves the safety profile and safety margin for the patient.

Prior art iterations of cutting edges for needles or other lumens are shown in FIG. 19, which includes exploded inset views at the top. These illustrations are also reflective of European Patent No. EP0929330 B1 to Gravelee. Generally speaking, angled, cutting edge E2 is disposed at the distal end of needle/lumen E. In some embodiments, sharp leading portion of the cutting edge may be situated along the inner diameter of the lumen E rather than as shown on its outer circumference. In contrast to other conventional needles having a top edge E3 that substantially mirrors the bottom edge E2, top trailing edge E4 may be partially rounded (i.e., not as sharp as the cutting edge 38) along its inner diameter edge. This rounded trailing cutting edge E4 allows the tissue to be punctured without a plug of tissue from being cut out by the trailing cutting edge of the needle which might then be injected into a patient's tissue or into the blood stream and possibly cause a downstream embolus (blockage of a blood vessel) or an abscess. in this configuration, the partially rounded edge E4 of the needle E extends around 1% to 60%, and preferably to about 50% of the circumference of the needle E. Notably, a substantial portion of the cutting edge of E4 is still flattened, presumably to facilitate the cutting action, so that both edges E3 and E4 present a potential "pinch point" in the event needle E were used as an inner sheath. In both illustrations of FIG. 19, the leading cutting edge E2 makes a curvilinear or an arc shaped cut through the tissue, with the resulting curvilinear incision in a blood vessel sealing and healing much more readily than if a tissue plug has been removed.

As seen in FIG. 20A (including an exploded inset of the trailing edge R4) through 20C, the introducer system has a more fully rounded edge R4 or transition between the inner diameter of the lumen R and the outside surface along a portion of the trailing edge R4 of curvilinear opening R6. Lead cutting edge R2 is disposed along the opposing side of opening R6. This attribute is a significant advantage, particularly at the heel or trailing edge of the bevel, where the lead anchor (not shown) is bent or flexed during part of or all of the development, manufacture, assembly, delivery, use, insertion, positioning, and/or repositioning in tissue. By rounding this region of the needle (and/or other areas where the electrode bends or flexes at an acute angle while potentially making contact with an edge surface), the sharpness of the edge is reduced so as to completely eliminate any edge which could, cut, severe, nick, create an unwanted notch, or otherwise damage or impair the function of the lead which can and/or will contact the heel of the bevel. Another desirable attribute of the present invention is that it can combine the bevel with the rounded edge so that it enables insertion of the introducer and lead into the tissue without risking damage to the lead while maintaining a sufficiently sharp (e.g., not blunt) leading edge and interface enabling it to advance through tissue.

As seen in FIG. 20C, the fully rounded edge can also be reproduced along any portion of the edge R14 associated with the slot R16 through which the distal end of the electrode (not shown) may be restrained. In contrast, edge R12 could be fully rounded, or it could more closely mimic the sharper cutting edge of leading edge R2. Slot R16 may have a similar curvilinear shape in comparison to opening R6, although it is possible to form slot R16 as an elongated, oblong, slit-like, or polygonal shape situated offset from, parallel to, or orthogonal with the axis defined by the cylindrical shape associated with needle R.

The fully rounded aspect of the needle or edge which is rounded in the prior art is different from the rounded edge in the present invention. The prior art describes edge E4 as extending only along the inner circumference of the needle, thereby retaining a pinch point (albeit one with a slight less sharp edge). In contrast, rounded edge R4 that extends from the inside to the outside of the needle (i.e., to retain a substantially constant diameter relative to the arc formed by the rounded edge), thereby distributing force applied to the electrode evenly along the entire surface of the edge R4. In another embodiment, the round edge R4 is orthogonal or perpendicular to the circumference of the needle (i.e., the edge that extends from the inner to the outer diameter), thereby encompassing oval shapes whose radius may vary. In both instances, edge R4 creates a smooth transition that is devoid of any pinch points, and the term fully rounded encompasses both constant radius arcs as well as ovals.

As a further example of differences between the prior art and the present introducer, the goals of the prior art and the present invention are different. The prior art is designed to enable insertion into a blood vessel, whereas the introducer described herein intentionally attempts to avoid contact with blood vessels and, instead, is designed to penetrate tissue proximate to nerves. The prior art is also designed to avoid cutting a plug of tissue, whereas the fully rounded edge is designed to avoid or reduce damage to a self-anchoring electrode before and during lead placement, testing, re-positioning, and/or deployment procedures.

In contrast to prior art, the fully rounded edges or surfaces in locations contacting or of potential contact with the lead to eliminate or reduce risk of lead damage, which could increase risk of lead fracture. The use of fully rounded edges effectively eliminates edges or sharp edges, increases the reliability and performance of the lead, and improves the safety profile and safety margin for the patient.

Tuohy needles and modified Tuohy needles known in the art have a dulled bevel to enable catheters to be passed through them more safely. Such catheters possess a substantially larger diameter, insofar as they must accommodate fluid flow without creating blockages. In contrast, the introducer system is not designed for catheters and, instead, employs a desirably thin gauge needle with an inner diameter (e.g., lumen) that is only large enough to accommodate a fine wire lead so as to enable the system to penetrate and advance through tissue. As such, Tuohy needles are incompatible with the design intent of the introducer system, and their excessive diameter would create difficulties in accommodating a lead without excessive movement and potential damage to the lead. Further, the distal anchor of the lead rests against the heel of the bevel in a way that enables the introducer to maintain the position and location of the lead relative to the introducer as it is manipulated within human or animal tissue.

The present system for the percutaneous placement of a small-diameter coiled lead also reduces the risk of accidental lead dislodgement. This object of avoiding lead dislodgement is achieved with self-anchoring, migration and infection resistant small-diameter coil/helix leads. Further, these advantages are particularly useful (in comparison to previous systems) during the initial period of time in which the lead is left in place within the desired tissue (e.g., in the time period prior to complete encapsulation of the lead within connective tissue, or from 1 day to several months of indwelling). Other advantages (possibly in addition to others noted herein) include the ability to enable the duration of the lead placement and stimulation testing procedures to be minimized; a reduction in the number of percutaneous insertions required; a decrease risk to the patient by enabling efficient positioning and re-positioning of the lead for stimulation testing and correct/optimal lead deployment by clinicians with minimal or no additional training, as well as by decreasing the time required to form electrical connections for testing. Therapy may be delivered to patients by clinicians in settings/scenarios that were previously burdensome, not practical and/or not possible (e.g., to treat pre-operative, pen-operative, and/or post-operative pain).

In certain embodiments, accidental lead dislodgement is also avoided by relying on an anchoring mechanism made from a bioabsorbable material (e.g., Poly glycolic acid: Trimethylene carbonate, Polylactic acid, or other appropriate bioabsorbable material with sufficient mechanical properties to act as an anchoring mechanism) at least in portions of the lead/electrode. The use of such a bioabsorbable anchor(s) facilitates fixation of the lead in the tissue, avoiding accidental dislodgement. Use of such an anchor(s) can also be designed such that as the lead becomes encapsulated/secured by tissue growth, the anchor(s) become absorbed, thereby reducing the risk of fracturing the lead upon removal at the end of the active therapy. Over time, the biosorbable portions are then accommodated naturally by the body, leaving only the stimulation portions of the lead securely in place.

Monofilaments of material (e.g., similar to dissolving sutures) may supplement the distal anchor(s), along with any number of optional barbs, in order to help with short-term fixation. These filaments and/or barbs may have varying or consistent geometry, including various shapes and thicknesses that can be made using conventional molding. These tips may be attached by integrating mechanically with the lead by a number of appropriate methods, examples of which include integration within the open coil of the lead, by overmolding the lead, or by covering the existing insulation coating of the lead with a secondary extruded layer of bioabsorbable material. Additionally, bioabsorbable tips may be attached to the lead through a hot melt approach (using an absorbable material as the adhesive). Such approaches allow the present invention to enhance short-term fixation and avoid accidental dislodgement while using or placing a self-anchoring, migration and infection resistant coiled/helical lead. These biosorbable aspects may be used alone or, advantageously, in combination with one or more aspects of the present invention described elsewhere in this disclosure.

With reference to FIG. 12A, once the lead is placed in the patient, the introducing device may be disengaged and removed. A proximal portion of the lead 934 may then be engaged with a lead connector unit 950 as indicated by the arrow. The lead connector 950 may have an insulation displacement connector (IDC) (not shown in FIGS. 12A and 12B) and a groove 952 configured to receive a lead 934. The groove 952 may comprise a contact strip with receiving members (e.g., micro-structure barbs, snaps, magnets, etc.) (not shown) to hold the lead 934 in place.

Another embodiment of the lead connector that eliminates the need for a separate tool as it can allow for a one-handed push mechanism for the clinician and/or patient is shown in FIG. 12B. The lead (not shown) is received in the aperture 952, which may have a conical, funneled, or cylindrical shape terminating in the connection point of the main housing of unit 950. The lead connector unit 950 may also include a break-away connection, e.g., the lead connector end 954 includes a magnet with the opposing end of the lead connector cable end 956 having an oppositely charged magnet (mated in the embodiment shown in FIG. 12B), allowing a clinician, patient, etc., to easily disconnect the cable 958 from the unit 950. This magnetized or other type of connection can be integrated anywhere along the body of unit 950. The connection mechanism also contemplates other removable connection types, including snaps, adhesives, clips, Velco®, force fittings, or any other appropriate means of connection.

Additionally or alternatively, the connector 950 may have a rotating element, such as a knob, dial, spool or post 953. The rotating element may engage the lead, mechanically and/or electrically, in order to assist in adjusting the tension of the detachable connection having tension formed by the electrode, the lead connector and the lead. The rotating element may include a predetermined tension release or recoil mechanism that responds to a disconnection force by releasing excess lead that is wound around the element. In the same manner, the lead connector 950 may accomplish this tension release by slider or other movement that need not be rotational in nature. As with the detachable aspects of the lead connections, the tension release may occur at a force that is less than or equal to one-half the force required to dislodge or move the electrode from its initial position.

The IDC mechanism may assist in connecting the lead 934 into the groove 952 in order to enable the connection between the receiving members and the lead 934. In this embodiment, the clinician relies on his or her dominant or non-dominant hand to insert and connect the lead. The IDC mechanism may also be capable of stripping any insulation from the lead 934 in order to establish better electrical contact between the lead 934 and the unit 950/groove 952. The IDC may be formed integral with or separately attached to the lead connector unit.

Exemplary alternative embodiments of the IDC are depicted in FIGS. 21A and 21B. IDC 989 shown in FIG. 21A may include a drawer type mechanism 990, such as a pivoting disc that rotates relative to pivot point PP and in the pivoting direction indicated by arrow PD, that is insertable into the body of the IDC and removable therefrom. A slot 952, similar in function to that described in FIG. 12A, bisects a portion of the disc. Slot 952 has an appropriate shape and size to firmly engages the lead within the disc and may include slidable portions, jaws, barbs, or the like. Disc 990 rotates so that the proximal end of the lead is fully inside the IDC 989 while the other portion protrudes out of the unit 989. Springs, locks, and guiding mechanisms may also be provided to afford better control of disc 990 when in operation.

In another embodiment shown in FIG. 21B, an IDC 1089 may have a generally cylindrical shape. The IDC 1089 may include an aperture, slot or opening 1990 into which the lead may be inserted (similar to the function and features associated with slot 952 above). The IDC 1089 may include an actuating lever AL to twist or rotate the body of IDC 1089 relative to the portion containing the slot 1090 (i.e., as indicated by pivot direction arrow PD) so that the lead is secured inside the IDC 1089. Barbs (not shown) may be included in the interior of the IDC 1089 if necessary to remove insulation from the lead to expose the underlying wire. Cooperating guides or grooves (not shown) may facilitate to the relative motion of the bodies 1089, 1090, and stops and locking mechanisms may also be included to prevent accidental motions.

The lead connector 950 may be bifurcated to receive a plurality of leads 934. For example, multiple slots or funnels can connect multiple leads to a single stimulator to enable therapeutic stimulation to be provided to separate parts of the body.

The connection between the lead connector 950 and electrode 934 may be detachable. The detachability may include, without limitation, magnets, such as insert molded neodymium magnets, that may be formed on the connector and one or both ends of the lead (if on both ends, the stimulator would also have a detachable connection as described herein). Depending on the manufacturing process, the magnets, and how the magnets are fitted together, may allow for differentiating the points of connections. For example, the lead connector may have a stepped connection port that fits with a correspondingly stepped connection on one of the lead, as illustrated in FIG. 22A. Alternatively, a circular magnet may sit on the top of the connector lead, also shown in FIG. 22B. A slight indentation or groove or other releasable force fitting could be provided to allow for the experience of a "snap-in" feel.

Figure 22C:
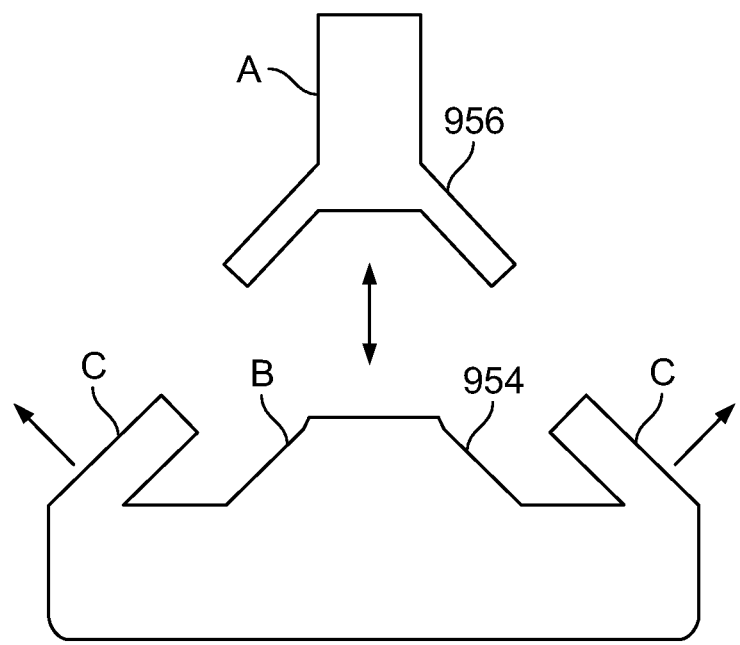

In addition to or in place of magnets, a spring-loaded fitting could be used. An example of such a fitting is shown in FIG. 22C. The fitting is described generically so that it may be employed on any of the components, although particular utility is expected at the connection between the lead connector 950 and the electrode 934. End A has an inverted Y shape that mates with a corresponding shaped end B. Additional shapes, prongs or members may be included. The outermost arms C move, preferably in a spring-loaded or magnetic fashion, to receive and release end A (single ended arrows indicate a preferred range of motion). Ends A and B may be fitted in the plane parallel to the double arrow and/or they may be dropped or snapped into place and then released in a direction that is different than, preferably including perpendicular to, the direction of release.

In some embodiments, the lead connector and lead may include a detachable connection configured such that neither the stimulator not the lead are displaced if unwanted force is applied to them or their connection(s). For example, the connection between the lead and the stimulator may be detachable upon application of a predetermined force. The predetermined force may be calculated to generally prevent movement of the electrode once placed in the appropriate position within the patient.

Alternatively or in addition the lead may itself be detachable (e.g. in the middle so that it actually is a plurality of leads, e.g., two or more). The lead may be detachable at any point between the lead and the stimulator, e.g., lead may disconnect at either end. Further still, the predetermined detachable portion may be between the lead and stimulator, along any portion of the length of the lead. For example, two or more leads could be selectively attached at a detachment point to disconnect upon application of the predetermined force. Further, while the present disclosure notes that the portions are detachable, they may also be re-attachable. This may allow the system to serve as a failsafe mechanism to prevent damage and/or injury to the system, components, and/or the patient.

In addition to just safely detaching, the circuitry in the lead (and/or other components, such as the lead connector) may prevent delivery of unwanted stimulation in the event of a disconnection during stimulation. By way of a non-limiting example, the lead may be a "smart lead" that has components in addition to a path for electrical conduction that minimizes the risk of the patient experiencing unwanted stimulation (e.g., minimizes or eliminates the potential for the patient to experience a shock) when the lead is disconnected unexpectedly during use.

All of the above-mentioned connections rely on mated parts. In order to avoid improper installation, each of the mated pairs could be given a unique shape. Sensors or other circuitry could be employed at the connections points to better enhance the user alert feature described herein. Such sensors or circuitry could be inherent to the electrical signal delivering the stimulation, or separate signals could be established.

Figure 22D:
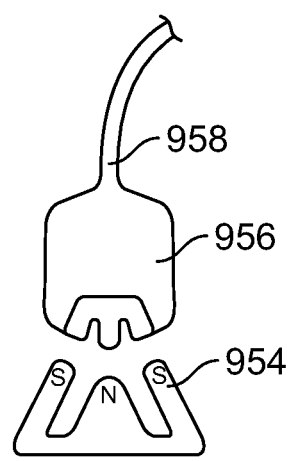

In an embodiment, as shown in FIG. 22D, the connection may be comprise a lead connector lead end plug with at least two-prongs or three-prongs of steel electrical contract that attract to the magnetic armature of the lead connector end.

The lead may optionally couple with the stimulator (not shown). The stimulator may comprise a battery (not shown), a programmable memory unit, and circuitry necessary to deliver the therapeutic stimulation inherent to the system. In an embodiment, the battery may be embedded within the lead connector or another electrode. The battery may be thin, flexible, and powerful. The battery may contain a charge for use of at least 24 hours to maximize use without charging or replacement. The stimulator may also contain a graphical user interface to communicate with the patient and/or clinician. It may contain LED or other visual indicia to communicate actions, errors, or other pertinent information about the operation of the stimulation system. The stimulator may allow for patient and/or clinician adjustments for the operation of the system. Additionally, the stimulator may be worn on a patient's body thereby minimizing cables and making the system easier to wear than conventional external stimulators. The stimulator may also be waterproof for ease of all-day wear.

Additionally, the introducing device may be paired with a custom bandage system that minimizes the risk of lead dislodgement during use. As shown in FIG. 23, the lead 1034 and lead connector unit 1050 may be protected and attached to the patient with a custom bandage 1060. The bandage 1060 may eliminate the need for a separate tape to secure the lead 934 and lead connector 950. The bandage 1060 may integrate with the lead connector unit 1050 to allow the clinician and/or patient to easily and consistently remove and replace the bandage 1060 without fear of inadvertently pulling the lead and/or otherwise dislodging it. The bandage 1060 may be comprised of the same film materials used in standard bandages, e.g., aperture or non-apertured films, including, but not limited to any polymeric material including, but not limited to polyethylene, metallocene catalyzed polyethylene, polypropylene, polyolefin copolymers, and ethylene vinyl acetate copolymers. The bandage 1060 may also comprise adhesive material. Suitable adhesives may include, but are not limited to, acrylic based, dextrin based, and urethane based adhesives as well as natural and synthetic elastomers. The adhesives may also include amorphous polyolefins including amorphous polypropylene. In an embodiment, the bandage 1060 may have an adhesive perimeter 1062 including optional removal tabs 1064. The adhesive perimeter 1062 may prevent the lead 1034 from being exposed to any adhesive surfaces and inadvertently being attached to the bandage 1060. The center of the bandage 1060 may include an absorbent pad 1066 configured to cover the entry point of the lead 1034 into the patient. The absorbent pad 1066 may be configured to absorb any fluid exiting the lead insertion site, e.g., any kind of liquid (including, without limitation, blood, pus) that may ooze from the lead insertion site. The size of the pad 1066 may allow a patient and/or clinician to view the area around the lead exit site to determine the existence of any infections or abnormalities. The absorbent pad 1060 may be surrounded by a clear polyethylene section 1068 of the bandage 1060 that allows for the clinician and/or patient to be able to better see the placement of the bandage 1060. A cutout 1070 in the adhesive perimeter 1062 of the bandage 1060 overlies the lead connector 1050, eliminating gaps in the bandage seal, but allowing for direct contact between a clinician and/or patient with the lead connector 1050 during the removal/attachment process. During removal, a patient and/or clinician can put his or her finger over the pad 1066 and the lead connector unit 950 to generally prevent the lead 934 from pulling the patient's skin. This may be particularly useful in difficult to reach position on the patient's body and on body parts with frequent movement, e.g., arms, legs, back, head, etc.

When applying or changing the bandage 1060 as shown in the FIGS. 24A through 24F, a clinician and/or patient may disconnect the lead connector cable 1056 from the stimulator (not shown) and apply a temporary tape strip 1072 to apply pressure to the lead connector 1056. The clinician and/or patient may apply additional pressure to the lead connector 1056 while removing the bandage 1060 from the patient. The site may then be inspected and cleaned. A new bandage may be applied to the site, the temporary tape strip 1072 may be removed, and the lead connector 1050 may be reconnected to the stimulator.

The present teachings are not limited to any specific treatment or indication. The system may apply to any kind of treatment, including, without limitation post-surgical pain patients or any type of pain patients, especially chronic pain patients (e.g. neuropathic pain, headache, and/or back pain patients).

A lead connector unit may include a lead storage mechanism to store excess portions of the lead (e.g., while the lead is coupled to the lead connector). This mechanism may reduce the excess length of lead between the lead connector and the point from which the lead exits the body. This may reduce the risk of the being caught on an object and being pulled and/or breaking. If the lead is caught, for example, on an external object or from a body part, then the excess lead stored on the mechanism may be released rather than dislodging or moving the lead from the tissue, fracturing the lead (inside or outside the body), and/or pulling the lead out and decoupling from the lead connector. In a non-limiting example, the mechanism may be a spool around which the lead is wound, either manually or automatically (e.g., using a spring). In another non-limiting example, the mechanism may be located on the outside of the lead connector or within the lead connector. In addition, the lead connector may be padded on one or more sides to provide comfort while wearing the lead connector.

The lead connector may also be designed to couple to the stimulator easily, and may enable connection using a single hand, such as by way of a magnetic connection as noted herein. It should be understood, however, that while a magnetic connection is described, the connection maybe any mechanical connection in addition to or alternatively to the magnetic connection. The connection may be oriented at various angles with respect to the surface of the skin. In a non-limiting example, the connection is oriented generally perpendicular to the skin. In another non-limiting example, the connection is generally parallel to the surface of the skin. In yet another embodiment, the connection may be easy for the user to make (e.g., does not require great dexterity, may be connected even without looking at the connectors) and strong enough to prevent inadvertent disconnection (e.g., due to common body movements or small forces, etc.) while disconnecting when subjected to stronger forces that may dislodge the lead (e.g., from external objects or body parts pulling or tugging on the lead connector or stimulator attached to the lead connector). The connection may prevent the lead from dislodging or fracturing by disconnecting the lead connector and lead when the lead is pulled rather than transmitting the force along the lead. In a non-limiting example, the magnetic connectors may be structured such that the surrounding magnetic field is reduced and avoids interfering with objects placed near the magnetic connectors (e.g., credit cards, cell phones).

Further still, the lead may connect directly to the stimulator (i.e., lead connector may be built into or integrally with the stimulator). The stimulator may be placed directly over or adjacent to the lead exit site to protect the exit site. There may be a clear window through which the lead exit site can be monitored for safety (e.g., infections, irritation).

In another non-limiting example, the lead may connect to the lead connector using a jack and plug, and the jack may be located on the lead and oriented at an angle (such as 90 degrees) to the lead. This jack may be connected to the plug on the lead connector using a downward force, enabling connection using a single hand. The very small distances between the magnetic armature of the plug and the permanent magnet structure of the lead connector means that the residual field outside the lead connector is very small as shown in FIG. 26.

A cable may attach to the stimulator and stored or organized (e.g., wound, coiled, wrapped around) to reduce the length of the lead (or lead) that may become caught, for example, on an external object or a body part. In a non-limiting example, the excess cable may be stored in a storage device attached to the cable, on the lead connector, and/or on the stimulator. In a non-limiting example, the storage device is a spool around which the cable may be wound manually or automatically (e.g., via a spring). In an embodiment, the cable may be coiled or wound around a spool on the stimulator, and forces on the lead cause the cable to be uncoiled from the spool rather than disconnect from the stimulator, transmit the force to the lead connector, and/or cable.

The stimulation system may contain lead that attach to the stimulator available in multiple lengths. In a non-limiting example, the lead with the shortest length that enables connection between the stimulator and the lead connector may be selected to reduce the risk of the lead catching on an object or body part and disconnecting the system, dislodge the lead, and/or fracture the lead.

In some embodiments, the stimulator may enable coordinated stimulation across two or more stimulators. In the alternative or in addition, the controller and/or programmer unit may enable coordinated stimulation across two or more stimulators. Coordinated stimulation may enable stimulation across multiple stimulators to start and stop in a coordinated manner to avoid asynchronous activation of muscle on opposite sides of the body (e.g., the back or torso), which may cause loss of balance or discomfort. Control over stimulation across multiple stimulators may also prevent synchronized stimulation, for example, to avoid activation of opposing muscles (e.g., biceps and triceps), which may cause discomfort. In a non-limiting example, one of the stimulators, controller and/or programmer unit may communicate with other stimulators directly. In another non-limiting example, each stimulators may be connected to a central controlling unit, which may be another stimulator or may be a non-stimulating control unit. In a non-limiting example, communication among stimulators and/or control units (controller or programmer unit) may be wireless (e.g., via Bluetooth, Wi-Fi) or wired (e.g., cables).

A battery-operated, body-worn stimulator may generate electrical current that may be administered via the lead and/or introducer. In one embodiment, the stimulator is a small pod (e.g., with rounded contours and of minimal profile height) that is worn on the body via a gel patch electrode that serves as the return electrode and is connected with two snaps that also provide electrical connection. In one embodiment, the stimulator has a minimal user interfaces (e.g., a press button start/stop, LED lights and a speaker or buzzer) to provide critical feedback to the patient. For example, the lights may blink or light up (e.g., different colors or different flashing patterns) if the battery is low or if there is a problem with stimulation. This important feedback will alert the patient or clinician to address any issues, such as battery failure, gel pad detachment, or open connection. In the non-limiting example with a magnetic lead connector, it is important that the stimulator produces an alert if the quick-release cable is accidentally dislodged without the patient's knowledge. Additionally, lead errors that cause stimulation to stop due to, for example, high electrode impedance issues (e.g., due to lost connection between skin and return electrode), and can impact therapy usage time and therapeutic benefit received by the patient and the audible or visible alert of the stimulator prevents this. Further, in one embodiment, the stimulator memory will generate an activity log for documenting usage of the stimulator and errors during therapy. The stimulator log may include a list of errors that occurred, along with timestamps of the time that errors occurred, a history of usage time, including amplitude and stimulation parameter settings used. These features are important to ensure that patients are able to effectively use the stimulation and that clinicians can effectively monitor their stimulation usage.

An additional embodiment of a breakaway mechanism is shown in FIGS. 25A through 25D. In FIG. 25A, a portion of the breakaway mechanism is shown as a receptacle portion, including wire/lead contact point CW. The receptacle portion may include a magnet M of any appropriate embodiment that includes a contact point. The receptacle portion may include an iron magnetic stator 1110, which may act as a pathway keeper. FIG. 25B depicts a mating portion of the breakaway mechanism, which is a plug 1112. The plug may include an iron magnetic keeper path 1113 and a contact 1114. The lead may be operatively attached with the plug 1112.

As shown in FIG. 25C, the breakaway mechanism may include a spring loaded plunger mechanism PM. The plunger mechanism utilizes a pair of biasing members BM that may push plungers toward each other as the plug is inserted into the receptacle. This may secure the breakaway mechanism together. The force utilized to keep the breakaway mechanism together is defined such that any amount of force applied to the system that exceeds such force will cause the plug to separate from the receptacle, e.g., if there is a force applied to the lead because it snags on something. This will generally protect the system. In particular, it generally prevents the lead and/or electrode from becoming disengaged or moved from their intended position.

Although the embodiments of this disclosure have been illustrated in the accompanying drawings and described in the foregoing detailed description, it is to be understood that the present disclosure is not to be limited to just the described embodiments, but that the embodiments described herein are capable of numerous rearrangements, modifications and substitutions without departing from the scope of the claims hereafter. It is, of course, not possible to describe every conceivable combination of components or methodologies for purposes of describing the present specification, but one of ordinary skill in the art may recognize that many further combinations and permutations of the present specification are possible. Each of the components described above may be combined or added together in any permutation to define an introducing device and/or introducing system. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The claims as follows are intended to include all modifications and alterations insofar as they come within the scope of the claims or the equivalent thereof.

The invention claimed is:

1. An introducer system for positioning, testing, and deploying a lead for percutaneous peripheral nerve stimulation, the system comprising:
   an electrical stimulus generator unit;
   a needle assembly including an outer sheath having an outer circumference and defining a lumen, an inner sheath carried completely within the lumen during positioning and testing, and a plurality of test electrodes positioned along the outer circumference and electrically communicating with the stimulus generator unit;
   a self-anchoring open-coiled helical stimulation lead carried within the inner sheath and having a conductive distal anchor, said anchor comprising an integrated electrode, and a proximal end in communication with the stimulus generator unit,
   a deployment mechanism cooperating relative to the lead and the needle assembly to deploy the lead out of the needle assembly at a selected position identified by at least one of the plurality of test electrodes during positioning and testing of the system; and
   wherein the self-anchoring lead remains confined within the needle assembly prior to deployment of the self-anchoring open-coiled helical stimulation lead and the distal anchor remains deployed in tissue after deployment of the self-anchoring open-coiled helical stimulation lead.

2. The system of claim 1, wherein the deployment mechanism is selected from a plunger and a spacer.

3. The system of claim 1, wherein two or more test electrodes are provided as an array spaced axially along the outer circumference.

4. An introducer system for positioning, testing, and deploying a lead for percutaneous peripheral nerve stimulation, the system comprising:
   an electrical stimulus generator unit;
   a needle assembly including an outer sheath having an outer circumference and defining a lumen, an inner sheath carried completely within the lumen during positioning and testing, and a plurality of test electrodes positioned along the axial length of the outer circumference of the outer sheath at spaced-apart intervals and connected to the stimulus generator unit;
   a self-anchoring open-coiled helical stimulation lead carried within the inner sheath and having a distal anchoring electrode through which stimulation can be delivered and a proximal end in communication with the stimulus generator unit,
   wherein at least one spacer is movable along an axis of the needle assembly so as to retract the outer sheath at intervals that correspond to one or more positions of the test electrodes; and
   wherein the self-anchoring lead is deployed at one of the selected locations of one of the test electrodes as desired.

5. The introducer system according to claim 4 further comprising a quick disconnection mechanism for maintaining contact between the proximal end and the stimulus generator unit.

6. The introducer system according to claim 5, wherein the quick disconnection mechanism includes at least one aperture or slot and wherein a proximal end of the electrode is received in the aperture or slot.

7. The introducer system of claim 6, wherein the needle assembly can be repeatedly repositioned without deploying the lead.

8. The introducer system according to claim 5, wherein the quick disconnection mechanism includes at least one magnet.

9. The introducer system of claim 8, wherein, as the lead is deployed from the needle assembly, the distal anchor is exposed from the needle assembly and anchors at one of the desired positions.

10. The introducer system according to claim 5, wherein the quick disconnection mechanism includes an insulation displacement connector.

11. The introducer system according to claim 5, wherein the quick disconnection mechanism includes at least one biasing member.

12. The introducer system of claim 5, wherein, when a test mode of the stimulus generator unit is activated, the at least one test electrode delivers test stimulation at one or more desired positions.

13. An introducer system for positioning, testing, and deploying a lead for percutaneous peripheral nerve stimulation, the system comprising:
   an electrical stimulus generator unit;
   an open-coiled stimulation lead having a conductive distal anchor and a proximal end in communication with the stimulus generator unit,
   a needle assembly including an outer sheath having an outer circumference and defining a bore, an inner sheath carried completely within the bore during positioning and testing, and at least one test electrode positioned along the outer circumference and electrically communicating with the stimulus generator unit;
   wherein the lead is carried with the inner sheath until the lead deployed.

* * * * *